US012303572B2

(12) United States Patent
Lascola

(10) Patent No.: US 12,303,572 B2
(45) Date of Patent: *May 20, 2025

(54) ASCORBATE FORMULATIONS AND METHODS OF USE AS CONTRAST AGENTS

(71) Applicant: Duke University, Durham, NC (US)

(72) Inventor: Christopher David Lascola, Durham, NC (US)

(73) Assignee: Duke University, Durham, NC (US)

( * ) Notice: Subject to any disclaimer, the term of this patent is extended or adjusted under 35 U.S.C. 154(b) by 690 days.

This patent is subject to a terminal disclaimer.

(21) Appl. No.: 17/443,863

(22) Filed: Jul. 28, 2021

(65) Prior Publication Data

US 2021/0353780 A1 Nov. 18, 2021

Related U.S. Application Data

(63) Continuation of application No. 16/365,939, filed on Mar. 27, 2019, now Pat. No. 11,083,803, which is a continuation of application No. 15/461,759, filed on Mar. 17, 2017, now Pat. No. 10,286,089, which is a continuation of application No. PCT/US2016/054481, filed on Sep. 29, 2016.

(60) Provisional application No. 62/234,986, filed on Sep. 30, 2015, provisional application No. 62/291,138, filed on Feb. 4, 2016.

(51) Int. Cl.
A61K 49/06 (2006.01)
A61B 5/00 (2006.01)
A61B 5/055 (2006.01)
A61K 9/00 (2006.01)
A61K 9/08 (2006.01)
A61K 47/02 (2006.01)
A61K 47/26 (2006.01)
A61K 49/10 (2006.01)

(52) U.S. Cl.
CPC ............ *A61K 49/06* (2013.01); *A61B 5/0042* (2013.01); *A61B 5/0044* (2013.01); *A61B 5/055* (2013.01); *A61K 9/0019* (2013.01); *A61K 9/08* (2013.01); *A61K 47/02* (2013.01); *A61K 47/26* (2013.01); *A61K 49/10* (2013.01)

(58) Field of Classification Search
CPC .......... A61K 49/00; A61K 51/04; A61K 9/00; A61B 5/00; A61B 5/04
See application file for complete search history.

(56) References Cited

U.S. PATENT DOCUMENTS

| | | | |
|---|---|---|---|
| 4,639,364 A | 1/1987 | Hoey | |
| 5,260,050 A | 11/1993 | Ranney | |
| 5,624,661 A * | 4/1997 | Unger | A61K 49/08 424/9.364 |
| 5,985,245 A * | 11/1999 | Golman | A61K 49/18 424/9.361 |
| 6,278,893 B1 | 8/2001 | Ardenkj et al. | |
| 7,060,731 B2 * | 6/2006 | Juelsrud | A61P 43/00 564/507 |
| 9,655,983 B2 | 5/2017 | Meyer et al. | |
| 10,111,970 B2 * | 10/2018 | Lascola | A61K 47/26 |
| 10,286,089 B2 * | 5/2019 | Lascola | A61K 49/06 |
| 10,695,447 B2 * | 6/2020 | Lascola | A61B 5/0042 |
| 11,083,803 B2 * | 8/2021 | Lascola | A61K 49/10 |
| 11,235,074 B2 * | 2/2022 | Lascola | A61K 9/0019 |
| 2009/0297441 A1 | 12/2009 | Canham et al. | |
| 2011/0008252 A9 | 1/2011 | Hjelstuen et al. | |
| 2014/0154185 A1 | 6/2014 | Van Zijl et al. | |
| 2014/0234210 A1 | 8/2014 | Lin et al. | |
| 2014/0350193 A1 | 11/2014 | Axelsson et al. | |
| 2017/0189561 A1 | 7/2017 | Lascola | |

FOREIGN PATENT DOCUMENTS

| | | |
|---|---|---|
| CN | 102579329 A | 7/2012 |
| CN | 102757922 A | 10/2012 |
| EP | 0123314 A2 | 10/1984 |
| JP | H09227414 A | 9/1997 |
| JP | 2006181890 A | 7/2006 |
| JP | 2009227414 A | 10/2009 |
| JP | 2011145297 A | 7/2011 |
| KR | 19980701833 A | 6/1998 |
| WO | 9730736 A2 | 8/1997 |
| WO | 9811921 A2 | 3/1998 |
| WO | 03026786 A2 | 4/2003 |
| WO | 2005027954 A2 | 3/2005 |
| WO | 2006002873 A2 | 1/2006 |
| WO | 2014082958 A1 | 6/2014 |
| WO | 2015136538 A1 | 9/2015 |

OTHER PUBLICATIONS

European Office Action corresponding to 16784310.1; dated Mar. 16, 2022 (5 pages).
Canadian Office Action corresponding to Canadian Patent Application No. 2,997,791, dated Jun. 16, 2023 (4 pages).
Australian Patent Office Examination Report corresponding to AU 2018201339; mailed Dec. 4, 2018 (3 pages).
Biological Therapies. Product information—Sodium ascorbate solution 112,49 mg/ml. Jan. 1, 2011: 11 pp. Retrieved from the Internet Dec. 12, 2016 URL:http//www.hugogalindosalom.com/images/pdf/inserto.pdf; 9 pp.
Chinese Office Action corresponding to CN 201680003013.1; dated Mar. 20, 2020 (12 pages, including English Translation).
Chinese Supplementary Search Report corresponding to CN 201680003013.1 (2 pages).
European Examination Report corresponding to EP 16784310.1; dated Apr. 22, 2021 (7 pages).
European Patent Office Examination Report, EP 16779304.1, mailed Oct. 6, 2017.

(Continued)

Primary Examiner — Michael G. Hartley
Assistant Examiner — Jagadishwar R Samala
(74) Attorney, Agent, or Firm — Myers Bigel, P.A.

(57) ABSTRACT

A sterile aqueous composition suitable for use as an MRI contrast agent includes 100 to 600 mM ascorbate; and 100-600 mM sodium, meglumine, or a combination thereof. The composition preferably has an osmolarity of 200 to 1400 mOsm/L.

29 Claims, 11 Drawing Sheets

(56) References Cited

OTHER PUBLICATIONS

European Patent Office Examination Report, EP 16779304.1, mailed Feb. 26, 2018; 4 pages.
International Search Report and Written Opinion, PCT/US2016/054478, mailed Dec. 15, 2016.
International Search Report and Written Opinion, PCT/US2016/054481, mailed Dec. 14, 2016.
Material Safety Data Sheet. Ascorbic acid MSDS. Science Lab.com. 5 pages. Retrieved from internet May 24, 2017.
Meglumine. Wikipedia, retrieved Jan. 12, 2016, 1 page.
Office Action, U.S. Appl. No. 15/461,759, mailed Mar. 14, 2016, 9 pages.
Office Action, U.S. Appl. No. 15/461,759, mailed Mar. 14, 2018, 9 pages.
U.S. Patent and Trademark Office, Non-Final Office Action, U.S. Appl. No. 15/461,759, mailed Sep. 19, 2017.
Bors, W., et al., "Chapter 4: The vitamin C radical and its reactions. Vitamin C in Health and Disease", Edited by: L. Packer and J. Fuchs, Marcel Dekker, Inc., New York, 1997, 75-94.
Bushong, Stewart C., et al., "Chapter 24: Magnetic Resonance Imaging—E-Book: Physical and Biological Principles", Mosby, 4th Ed., 2014, 345-352.
Carver, J. P., et al., "A general two-site solution for the chemical exchange produced dependence of T2 upon the carr-Purcell pulse separation", Journal of Magnetic Resonance 6(1), 1972, 89-105.
Chan, Kannie, et al., "Natural D-glucose as a biodegradable MRI contrast agent for detecting cancer", Magnetic Resonance in Medicine 68(6), 2012, 1764-1773.
Chen, Qi, et al., "Pharmacologic doses of ascorbate act as a prooxidant and decrease growth of aggressive tumor xenografts in mice", PNAS 105(32), 2008, 11105-11109.
Hayashi, Koichiro, et al., "Superparamagnetic Nanoparticle Clusters for Cancer Theranostics Combining Magnetic Resonance Imaging and Hyperthermia Treatment", Theranostics 3(6), 2013, 366-376.
Hediger, Matthias A., "New View at C", Nature Medicine 8(5), 2002, 445-446.
Hills, B.P., et al., "N.M.R. studies of water proton relaxation in Sephadex bead suspensions", Molecular Physics 67 (1), 1989, 193-208.
Hoffer, L.J., et al., "Phase I clinical trial of i.v. ascorbic acid in advanced malignancy", Annal of Oncology 19(11), 2008, 1969-1974.
Jansen, Jacobus F.A., et al., "Tumor Metabolism and Perfusion in Head and Neck Squamous Cell Carcinoma: Pretreatment Multimodality Imaging With 1H Magnetic Resonance Spectroscopy, Dynamic Contrast-Enhanced MRI, and [18F]FDG-PET", Int J Radiat Oncol Biol Phys 81(1), 2012, 299-230.
Jasanoff, Alan, "MRI contrast agents for functional molecular imaging of brain activity", Current Opinion in Neurobiology 17(5), 2007, 593-600.
Lachapelle, Marc Y., et al., "Inactivation dates of the human and guinea pig vitamin C genes", Genetica 139(2), 2011, 199-207.
Lascola, Christopher D., et al., "MR contrast from ascorbic acid (vitamin C) in phantoms and in vivo. International Society for Magnetic Resonance in Medicine", 2010 ISMRM Meeting #40, May 1-7, 2010, Stockholm, Sweden.
Levine, M., et al., "Vitamin C pharmacokinetics in healthy volunteers: evidence for a recommended dietary allowance", PNAS 93(8), 1993, 3704-3709.
Liepinsh, Edvards, et al., "Proton exchange rates from amino acid side chains-implications for image contrast", Magnetic Resonance in Medicine 35(1), 1996, 30-42.
May, James M., et al., "Recycling of vitamin C from its oxidized forms by human endothelial cells. Biochim. Biophys. Acta. May 2003; 1640(2-3): 153-161", Biochimica et Biophysica Acta (BBA)—Molecular Cell Research 1640(2-3), 2003, 153-161.
Oreopoulos, D. G., et al., "Renal excretion of ascorbic acid: effect of age and sex", J Am College Nutr 12(5); Abstract Only, 1993, 537-542.
Rumsey, Steven C., et al., "Glucose Transporter Isoforms GLUT1 and GLUT3 Transport Dehydroascorbic Acid", J Biol Chem 274(30), 1997, 18982-18989.
Savini, I., et al., "SVCT1 and SVCT2: key proteins for vitamin C uptake", Amino Acids 34(3), 2008, 347-355.
Sreeja, V., et al., "Water-dispersible ascorbic-acid-coated magnetite nanoparticles for contrast enhancement in MRI", Appl Nanosci 5(4), 2015, 435-441.
Van Noorden, Richard, "Radioisotopes: The medical testing crisis", Nature 504(7479), 2013, 202-204.
Yadav, Nirbhay N., et al., "Natural D-glucose as a biodegradable MRI relaxation agent", MRM 72(3), 2014, 823-828.
Canadian Office Action corresponding to CA 2,997,791; dated Mar. 5, 2024 (3 pages).
Korean Office Action corresponding to KR 10-2018-7008638; issued Mar. 19, 2024 (14 pages, including English translation).

\* cited by examiner $K_{obs}$ (7.4) = 1.4 X $10^5$ $M^{-1}$ $s^{-1}$

THIS RATE CONSTANT INCREASES BY A FACTOR OF ≈10 WHEN PHOSPHATE IS PRESENT.*

T2WI FSE

2 MIN        10 MIN

T2WI

RARE T2 MAP

PRE DOSE        30 MIN

60 MIN        90 MIN

ASCORBATE FORMULATIONS AND METHODS OF USE AS CONTRAST AGENTS

RELATED APPLICATIONS

This application is a continuation of U.S. application Ser. No. 16/365,939, filed Mar. 27, 2019, which is a continuation of U.S. application Ser. No. 15/461,759, filed Mar. 17, 2017, which is a continuation under 35 U.S.C. 111(a) of PCT/US2016/054481, filed Sep. 29, 2016, which in turn claims the benefit of U.S. Provisional Patent Application Ser. No. 62/234,986, filed Sep. 30, 2015, and U.S. Provisional Patent Application Ser. No. 62/291,138, filed Feb. 4, 2016, the disclosure of each which is incorporated by reference herein in its entirety.

STATEMENT OF GOVERNMENT SUPPORT

This invention was made in part with government support under grant number W81XWH-Dec. 1, 0447 awarded by the Department of Defense. The United States government has certain rights in the invention.

FIELD OF THE INVENTION

The present invention concerns compositions useful for parenteral administration of ascorbate and radiological uses thereof.

BACKGROUND OF THE INVENTION

Magnetic resonance imaging (MRI) produces exquisite renderings of human anatomy and pathology at high spatial resolution. To increase diagnostic sensitivity and specificity for MRI, such as with imaging for cancer, infection, neurological and cardiovascular diseases, contrast material is often administered intravenously before and/or during imaging to improve signal.

The most common MRI contrast material is based on molecular complexes containing the paramagnetic metal gadolinium (Gd). Gd is a heavy metal that is found in nature only in combined (salt) form. In water-soluble salts it is highly toxic, but chelated Gd has reduced toxicity. In the U.S., all nine MRI contrast agents approved by the Food and Drug Administration (FDA) are Gd-based. Gd possesses strong "paramagnetism" that results in a locally increased MRI signal on $T_1$-weighted images. However, Gd-based contrast agents can cause a rare but severely debilitating condition called nephrogenic systemic fibrosis (NSF), a syndrome involving widespread fibrosis of the skin, joints, eyes, and internal organs. The World Health Organization and FDA have issued restrictions on the use of these Gd agents in patients with renal insufficiency/failure, with the FDA mandating a "black box" warning on all commercial contrast media containing Gd. As a consequence, millions of patients in the U.S., and many more worldwide, are no longer able to receive contrast material for MRI, severely limiting detection and characterization for several diseases. Additionally, in 2015 the FDA issued a drug safety communication indicating the agency is investigating the risk of brain deposits following repeated use of Gd-based contrast agents for MRI due to recent studies in people and animals demonstrating that Gd can remain in the brain, even in individuals with normal kidney, function.

Other paramagnetic complexes, used more rarely either as investigational or as "off-label," are usually based on large iron oxide-based nanoparticles developed and marketed as intravenous iron replacement therapy (e.g., FERAHEME® (ferumoxytol) injection). The use of these complexes for MRI is limited, however, by their large molecular size, which confines these agents to the subject's blood pool until they are finally cleared by the reticuloendothelial system (i.e., macrophages, liver, spleen).

U.S. Patent Application Publication 2014/0154185 to Van Zijl et al. discusses the use of parenteral glucose to enhance MRI. See also Yadav N N, Xu J, Bar-Shir A, Qin Q, Chan K W, Grgac K, Li W, McMahon M T, van Zijl P C, Natural D-glucose as a biodegradable MRI contrast agent for detecting cancer. Magn Reson Med. 2012 December; 68(6):1764-73; Yadav N N, Xu J, Bar-Shir A, Qin Q, Chan K W, Grgac K, Li W, McMahon M T, van Zijl P C, Natural D-glucose as a biodegradable MRI relaxation agent. Magn Reson Med. 2014 September; 72(3):823-28.

There remains a need for alternative/additional contrast agent compositions useful for MRI scanning technologies.

SUMMARY OF THE INVENTION

Provided herein are compositions useful in performing magnetic resonance imaging (MRI) including ascorbate (Vitamin C) as a contrast agent for the detection and characterization of perfusion, metabolism, and oxidative stress in human and non-human tissues, without the need for radioactivity or chemical labeling.

In some embodiments, a sterile aqueous composition, which may be suitable for use as an MRI contrast agent, is provided, said composition comprising: 100-600 mM ascorbate; and 100-600 mM sodium, meglumine, or a combination thereof (e.g., provided as meglumine ascorbate, sodium ascorbate, or a combination thereof) (e.g., 100-300 mM ascorbate) (e.g., wherein said composition comprises meglumine ascorbate and sodium ascorbate in a molar or millimolar (mM) ratio of from 10:90, 20:80, 30:70, or 40:60, up to 90:10, 80:20, 70:30, or 60:40 (meglumine ascorbate: sodium ascorbate)).

In some embodiments, the composition has an osmolarity of 200-1400 mOsm/L (e.g., 200-1200 mOsm/L).

In some embodiments, the composition further comprises carbonate and/or phosphate.

In some embodiments, the composition further comprises a reducing and/or a non-reducing sugar.

In some embodiments, the composition further comprises a stability agent (e.g., a chelator such as ethylenediaminetetraacetic acid (EDTA)).

In some embodiments, the composition is provided in unit dosage form.

Also provided is a powder composition comprising: ascorbate; sodium, meglumine, or a combination thereof (e.g., sodium ascorbate, meglumine ascorbate, or a combination thereof); optionally, carbonate and/or phosphate; and optionally, a reducing or non-reducing sugar. In some embodiments, the composition is in unit dosage form. In some embodiments, the powder composition, upon addition of a sterile liquid carrier (e.g., water, normal saline, lactated Ringers, or other aqueous vehicle suitable for parenteral drug delivery), is suitable to use in enhancing a magnetic resonance imaging (MRI) image of a body or body region such as an organ or organ region in a subject.

Upon parenteral administration, time-dependent magnetic resonance (MR) signal changes are detected in tissues and/or fluids where ascorbate is taken up and/or passes through. These MRI signal changes are detectable using routine spin echo or gradient echo-based $T_2$-weighted MRI sequences and are quantifiable with $T_2$ mapping. Other, less common acquisition techniques sensitive to spin-spin relaxation may also be used to encode MR signals.

Also provided herein are methods of enhancing an MRI image of a body or body region in a subject, such as an organ or organ region, which method includes parenterally administering (e.g., intravenous, intraperitoneal, intraarterial, intraosseous, or intrathecal administration) a parenteral ascorbate formulation to said subject in an MRI image-enhancing amount; and then generating, by MRI of the subject, an image of said body or body region, whereby the ascorbate or pharmaceutically acceptable salt thereof enhances the MRI image.

In some embodiments, the MRI image is generated during, or up to 5, 10, 30, 40, 60, 90 or 120 minutes after, or up to 1, 2, 3, or 4 hours after, the parenterally administering of the parenteral ascorbate formulation.

Further provided is the use of an ascorbate formulation as taught herein for carrying out a method as taught herein, or for the preparation of a medicament or imaging agent for carrying out a method as taught herein.

The present invention is explained in greater detail in the drawings herein and the specification set forth below. The disclosures of all United States patent references cited herein are to be incorporated by reference herein in their entirety.

BRIEF DESCRIPTION OF THE DRAWINGS

FIG. 1A, Ascorbate is a di-acid, however at physiological pH of 7.4, 99% of ascorbate is present as its mono anion (AscH$^-$). Ascorbate radical (Asc.$^-$) is present at equilibrium (but also at much lower concentrations) with oxidized and reduced forms of ascorbate. FIG. 1B, The dismutation of Asc.$^-$ is the principal route of its transformation, with a rate constant ($k_{obs}$) that falls into the "intermediate" proton exchange rate on the NMR timescale. This rate constant can increase by a factor of 10 in the presence of proton exchange catalysts such as phosphate (Bors W, Buettner G R. (1997) The vitamin C radical and its reactions in *Vitamin C in Health and Disease*, ed. by L. Packer and J. Fuchs, Marcel Dekker, Inc., New York, Chapter 4, pp 75-94).

FIG. 3A, shows quantitative $T_2$ mapping in 5 phantoms with progressively increasing ascorbate (AA) concentration. Statistically significant "negative $T_2$ contrast" (signal loss) is seen as low as 1-5 mM as compared to control (phosphate-buffered saline) with conventional fast spin echo (FSE) acquisition. Sensitivity is therefore at the lower end of expected tissue/cellular concentrations following pharmacological doses of ascorbate in high uptake tissues (e.g., tumors and brain, 10-30 mM). This result also does not take into account any synergistic effects from tissue oxidative substrates or physiological exchange catalysts. FIG. 3B, shows the synergistic effect of $H_2O_2$ on ascorbate $T_2$ enhancement. $H_2O_2$, which rises to 100-200 micromolar in brain and tumors in vivo following parenteral ascorbate, produces a marked synergism on the $T_2$ contrast effect from ascorbic acid. The synergistic effect slowly diminishes over time in phantoms over 30 min as shown, but will be sustained in vivo as long as $H_2O_2$ is produced following ascorbate administration. FIG. 3C, demonstrates the influence of pH on ascorbate's $T_2$ effect, which is maximized at neutral/physiological pH (7.0-7.4). This result is consistent with prior studies on the rate kinetics of ascorbate disproportionation with its radical and oxidized form at equilibrium (FIGS. 1A-1B). FIG. 3D, reveals a marked synergistic effect when ascorbate (Asc) is salified (salted) with meglumine (N-methyl-D-glucamine (MEG)), an amine sugar derivative of sorbital that is commonly employed as an excipient in several FDA-approved drug and contrast formulations.

FIG. 9A, shows a conventional single slice axial FSE T2WI image through the midbrain of a normal C57 black mouse, and the two images on the right demonstrate a 'first pass' extraction of contrast change during and following ascorbate administration i.v. $T_2$ signals in brain tissue are acquired immediately following, and 10 minutes after ascorbate administration, then subtracted from the T2 brain signals acquired before ascorbate administration. Since ascorbate produces a decrease in signal intensity, subtraction from the higher signal pre-dose scan results in a net positive 'map' of flow-through perfusion (blood flow) through brain tissue. At 10 minutes, the perfusion effect has nearly resolved and early signal intensity changes related to tissue uptake are beginning to be observed. FIG. 9B, shows the signal changes due to tissue uptake of high-dose ascorbate. Color-lute maps of signal intensity are not subtracted from the pre-dose scan and therefore show the expected decreases in T2 signal over time, maximized between 30-60 min in normal C57 mice.

FIG. 11A depicts the two primary imaging planes, coronal and axial, for rat heart imaging at 7T. FIG. 11B shows transient decrease in T2 signal intensity throughout the left ventricle with initial bolus of ascorbate injection i.v.

FIG. 12A, Fast spin echo (FSE) T2 images before and after 60 min slow infusion of ascorbate show dramatic signal intensity differences throughout the brain parenchyma. FIG. 12B and FIG. 12C respectively show normalized signal intensity changes and quantitative relaxivity measurements are shown for both guinea cerebral cortex (Cx) and basal ganglia (BG) after administration of three different ascorbate formulations.

DETAILED DESCRIPTION OF THE PREFERRED EMBODIMENTS

Figure 1A:
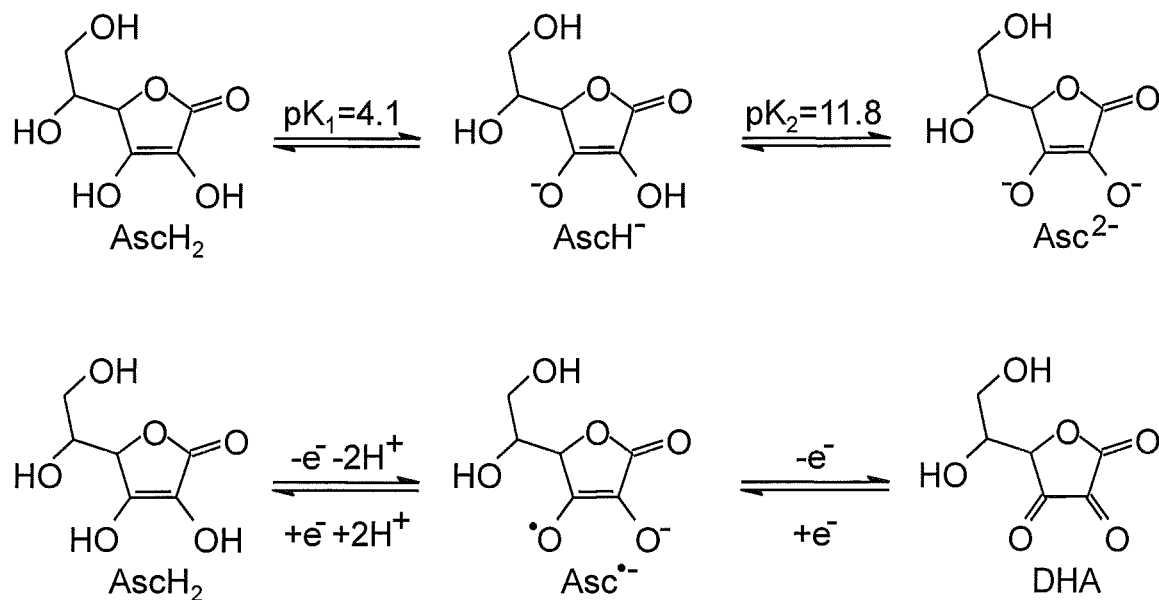
FIGS. 1A-1B. Ascorbate and dismutation of the ascorbate radical.

The present invention is now described more fully hereinafter with reference to the accompanying drawings, in which embodiments of the invention are shown. This invention may, however, be embodied in different forms and should not be construed as limited to the embodiments set forth herein; rather these embodiments are provided so that this disclosure will be thorough and complete and will fully convey the scope of the invention to those skilled in the art.

As used herein, the singular forms "a," "an" and "the" are intended to include plural forms as well, unless the context clearly indicates otherwise. It will be further understood that the terms "comprises" or "comprising" specify the presence of stated features, integers, steps, operations, elements, components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein.

Ascorbate. Ascorbate (also known as "ascorbic acid," "L-ascorbic acid" or "Vitamin C") is a naturally-occurring organic compound and an essential nutrient, with important properties as an antioxidant and co-factor in at least eight enzymatic reactions, including several collagen synthesis reactions that, when dysfunctional, result in the most conspicuous symptoms of scurvy. Most mammals make ascorbic acid in the liver, where the enzyme L-gulonolactone oxidase converts glucose to ascorbic acid. In humans, higher primates, guinea pigs and most bats, however, a mutation results in low or absent L-gulonolactone oxidase expression so that ascorbate must be consumed in the diet (Lachapelle, M. Y.; Drouin, G. (2010). "Inactivation dates of the human and guinea pig vitamin C genes". Genetica 139 (2): 199-207). In all animal species, L-ascorbic acid/ascorbate is the most abundant intracellular antioxidant, with intracellular concentrations capable of reaching 10-30 mM in tumors, brain cells, and some other tissues. Those tissues that accumulate over 100 times the level in blood plasma of vitamin C include the adrenal glands, pituitary, thymus, corpus luteum, and retina. Those with 10 to 50 times the concentration include brain, spleen, lung, testicle, lymph nodes, liver, thyroid, small intestinal mucosa, leukocytes, pancreas, kidney, and salivary glands (Hediger M A (May 2002). "New view at C". Nat. Med 8 (5): 445-6).

Dietary excesses of vitamin C are not absorbed, and excesses in the blood are rapidly excreted in the urine. Vitamin C exhibits remarkably low toxicity, with an $LD_{50}$ in rats generally accepted at ~11.9 grams per kilogram of body weight. The mechanism of death from such doses (1.2% of body weight, or 0.84 kg for a 70 kg human) is unknown, but may be mechanical rather than chemical ("Safety (MSDS) data for ascorbic acid". Oxford University. Oct. 9, 2005. Retrieved Feb. 21, 2007). The $LD_{50}$ in humans is uncertain given the lack of any accidental or intentional poisoning death data. The rat $LD_{50}$ is, therefore, used as a guide for human toxicity.

Figure 1B:
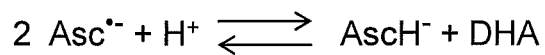

At physiological pH, 99% of ascorbate is present as the mono anion (FIG. 1A). The chemistry and therefore imaging properties of vitamin C are dominated by this moiety. As a donor antioxidant, the mono anion donates a hydrogen atom (H. or H$^+$+e$^-$) to an oxidizing radical to produce a resonance-stabilized tricarbonyl ascorbate free radical, Asc.$^-$ (FIG. 1B). The dismutation reaction of Asc.$^-$ back to reduced or oxidized ascorbate is the principal route of elimination in vitro. This process is supplemented in vivo by enzymes that aid in ascorbate recycling (May J M, Qu Z C, Neel D R, Li X (May 2003). "Recycling of vitamin C from its oxidized forms by human endothelial cells". Biochim. Biophys. Acta 1640 (2-3): 153-61). Dismutation of the radical to either ascorbate or dehydroascorbate occurs via loss or gain of hydrogen, which serves as either the electron carrier or the more conventional cation. Also, the rate constant of ascorbic radical dismutation is $10^5$-$10^6$ M$^{-1}$s$^{-1}$, so that hydrogen exchange accompanying dismutation also occurs at the same rate. On the NMR timescale, these "intermediate" exchange rates are optimal for altering $^1$H spin-spin relaxation.

Parenteral Formulations of Ascorbate. Ascorbate for parenteral administration may be provided in a pharmaceutically acceptable carrier (e.g., sterile water, endotoxin-free water, or pyrogen-free water; sterile, endotoxin-free or pyrogen-free saline, etc.) as a formulation suitable for parenteral administration. The term "pharmaceutically acceptable" as used herein means that the compound or composition is suitable for administration to a subject to achieve the treatments described herein, without unduly deleterious side effects in light of the severity of the disease and necessity of the treatment.

The formulations may be presented in unit/dose or multi-dose containers, for example sealed ampoules and vials, and may be stored in a dried/powdered/freeze-dried (lyophilized) condition requiring only the addition of the sterile liquid carrier, for example saline or water-for-injection immediately prior to use. Extemporaneous injection solutions and suspensions may be prepared from sterile powders, granules and tablets. For example, in one aspect of the present invention, there is provided an injectable, stable, sterile composition comprising ascorbate in a unit dosage form in a sealed container. The ascorbate may be provided in the form of a lyophilizate which is capable of being reconstituted with a suitable pharmaceutically acceptable carrier to form a liquid composition suitable for injection thereof into a subject.

Examples of suitable formulations include, but are not limited to, a sterile aqueous solution of ascorbic acid in water for injection, containing 10, 20, 30, 40, or 50, to 80, 90, 100, 150 or 200 mg/mL ascorbate or a salt thereof (e.g., sodium salt, meglumine (N-methyl-D-glutamine) salt, combinations thereof, etc.). In some embodiments, formulations may include 10, 20, 30, 40, 50, 60, 70, 80, 90, or 100 mM, to 150, 200, 250, 300, 350, 400, 450, 500, 550, 600, 650, 700, 750, or 800 mM ascorbate or a salt thereof (e.g., sodium salt, meglumine (N-methyl-D-glucamine) salt, combinations thereof, etc.). For example, formulations may include from 100 to 700 mM, or from 200 to 650 mM, or from 300 to 600 mM, or from 400 to 550 mM, ascorbate or a salt thereof. The ascorbate concentration may be adjusted as needed depending on the route of administration (e.g., intravenous administration versus direct administration into a localized body region or compartment).

In some embodiments, the pH is adjusted to approximately 7 (e.g., pH of from 6.5 to 7.5) (e.g., with sodium bicarbonate and/or sodium hydroxide).

Formulations suitable for parenteral administration may include a stabilizing agent. Example stabilizing agents include chelators such as EDTA (e.g., EDTA disodium). Formulations may also include pH buffers such as bicarbonate ($HCO_3^-$) and/or phosphate ($PO_4$).

Formulations according to some embodiments may include a sugar, such as a reducing or non-reducing sugar. A "reducing sugar" is an open-chain sugar having a free aldehyde group or a free ketone group, which includes all monosaccharides and some disaccharides, oligosaccharides and polysaccharides. Example reducing sugars include, but are not limited to, glucose, galactose, glyceraldehyde, fructose, ribose, xylose, lactose, maltose, etc. A "non-reducing sugar" is a sugar without a free aldehyde group or free ketone group. Example non-reducing sugars include, but are not limited to, sucrose, trehalose, etc.

The spin-spin exchange catalysts that may be used in the ascorbate formulations as taught herein may include, but are not limited to, meglumine (N-methyl-D-glucamine), reducing sugars (e.g., glucose, galactose, glyceraldehyde, fructose, ribose, xylose, lactose, maltose, combinations thereof, etc.), and non-reducing sugars (e.g., sucrose, trehalose, combinations thereof, etc.).

Formulations suitable for parenteral administration may have an osmolarity in the range of from 200 to 1200 or 1400 mOsm/L. In some embodiments, the formulation has an osmolarity of from 200, 300, 400, 500 or 600 to 700, 800, 900, 1000, 1100, 1200, 1300, or 1400 mOsm/L.

In some embodiments, the formulation is suitable for injection into an artery or vein, and/or into a body region such as an organ or organ region. In some embodiments, the formulation is suitable for intravenous infusion. In some embodiments, the formulation is suitable for intraarterial infusion. In some embodiments, the formulation is suitable for intrathecal infusion.

In some embodiments, the formulation is de-oxygenated. Methods of de-oxygenation of aqueous compositions are known, e.g., preparing the formulation under, or purging with, an inert gas, such as nitrogen. See, e.g., U.S. Patent Application publication 2014/0048290 to Bodemann.

In some embodiments, the formulation is provided as a dried/powdered/lyophilized composition of meglumine ascorbate, sodium ascorbate, or a combination of these salts, with or without exchange catalysts, chelators, etc., which may be reconstituted in sterile aqueous media (e.g., water, normal saline, lactated Ringers, or other accepted aqueous vehicle used for parenteral drug delivery) at point of care just prior to administration. Suitable dried formulations may include, but are not limited to, 5, 10, 15, 20, 25, 30, 35, 40, 45, 50, 55, 60, 65, 70, 75, 80, 85, 90, 95 or 100 grams of ascorbate of a salt thereof.

In some embodiments, the formulation is provided in a container suitable for light-sensitive liquid compositions, such as an opaque plastic or glass container (e.g., a high density polyethylene container, a plastic or glass container coated with black polyvinyl chloride, etc.), amber glass, etc. See, e.g., U.S. Pat. No. 8,309,191 to Wang et al.; U.S. Patent Application publication 2004/0048206 to Miyake et al.

In some embodiments, the formulation is provided in unit dosage form suitable for parenteral administration for MRI imaging. As non-limiting examples, unit dosage forms suitable for intravenous administration may be: 1) 0.25 g/min, up to 60 min, up to 15 grams; 2) 0.5 g/min, up to 60 min, up to 30 grams; 3) 1.0 g/min, up to 60 min, up to 60 grams; or 4) 1.5 g/min, up to 60 min, up to 90 grams.

Methods of use. As noted above, the parenteral ascorbate compositions as taught herein are useful for magnetic resonance imaging (MRI) to provide a contrast agent for the detection and characterization of perfusion, metabolism, and/or oxidative stress in human and non-human tissues, without the need for radioactivity or chemical labeling.

Ascorbate, especially in the presence of, and co-formulated with, spin-spin exchange catalysts (for example, simple sugars, sugar alcohols or amino acids) is a safe and biodegradable MRI contrast agent that requires neither the use of metal-based (e.g., gadolinium or iron) contrast material nor ionizing radiation. The technique enables assessment of tissue perfusion as well as high-resolution molecular characterization of tissue viability and metabolism that is analogous to $^{18}$F-FDG PET. The latter is possible by virtue of ascorbate's uptake (via dehydroascorbate) into cells through the same glucose transport mechanisms that take up $^{18}$F-FDG (i.e., GLUT 1 and 3 transporters) (Rumsey S C, Kwon O, Xu G W, Burant C F, Simpson I, Levine M (July 1997). "Glucose transporter isoforms GLUT1 and GLUT3 transport dehydroascorbic acid". *J Biol. Chem.* 272 (30): 18982-9).

"Parenteral administration" as used herein includes, but is not limited to, intravenous, subcutaneous, intramuscular, intraperitoneal, intraarterial, intraosseous, intrathecal or intraventricular administration, e.g., through injection or infusion. As a non-limiting example, intraperitoneal or other parenteral administration may be used where intravenous (i.v.) access is difficult for a subject (e.g., low blood pressure), or the route of administration otherwise would result in a suitable MRI image.

In some embodiments the MRI is performed during, or up to 5, 10, 30, 40, 60, 90 or 120 minutes after, or up to 1, 2, 3, or 4 hours after, parenterally administering the ascorbate composition.

Subjects benefitting from the present invention are, in general, mammalian subjects, including both human subjects and animal subjects (e.g., dogs, cats, rabbits, cattle, horses, etc.), for diagnostic, therapeutic, research or veterinary purposes. Subjects may be male or female and may be any age, including neonate, infant, juvenile, adolescent, adult, and geriatric subjects. MRI is known, and may be carried out by commercially available equipment, and by techniques known in the field. See, e.g., S. Bushong and G. Clarke, *Magnetic Resonance Imaging: Physical and Biological Principles* (Mosby, 4$^{th}$ Ed. 2014). In some embodiments, the MRI is perfusion (e.g., blood flow) imaging. In some embodiments, the MRI is metabolism imaging. Metabolism imaging may be used as a diagnostic biomarker analogous to $^{18}$F FDG PET, including, but not limited to, identification/characterization of tumors or dysfunctional tissues demonstrating hyper- or hypo-metabolism.

"Body or body region" that may be imaged with MRI as taught herein includes the body or any region of the body of a subject, such as an organ or organ system, soft tissue, bone, etc., or any portion thereof. Examples of body regions include, but are not limited to, head, neck, thorax, abdomen, pelvis, limb(s), muscle, fat, other soft tissues, bone, etc. Examples of organs include, but are not limited to, adrenal gland, pituitary, thymus, corpus luteum, retina, brain, spleen, lung, testicle, lymph nodes, liver, thyroid, small intestinal mucosa, leukocytes, pancreas, kidney, salivary gland tissue, heart, etc.

"Enhancing" an MRI image as used herein is inclusive of facilitating the MRI visualization by enhancing the contrast of structures, tissues or fluids in an MRI signal.

An "MRI contrast agent" is a substance that can enhance the contrast of structures, tissues or fluids within the body during an MRI scan. Examples include, but are not limited to, paramagnetic contrast agents such as Gd-containing agents or manganese chelates, and superparamagnetic agents such as iron platinum particles. See also U.S. Patent Application Publication Nos. 2014/0350193 to Axelsson et al.; and 2014/0234210 to Lin et al.

Potential applications for ascorbate MRI include several clinical scenarios where current medical practice often utilizes PET scanning but where improvements in methodology using MRI as an alternative scanning technology will potentially yield further clinical benefit. These scenarios include diagnostic studies for cancer, neurological disease (e.g., dementia, TBI and epilepsy) and cardiovascular imaging. Heart studies using Tc99m-labeled agents (e.g., Tc-99m sestimibi or "Cardiolite") represent a particularly noteworthy potential diagnostic application in need of an alternative approach given the projected contraction of supply of Tc-99m. Myocardial perfusion and viability imaging with Tc-99m-related agents is an essential and widely performed procedure, yet to date no commercially feasible solution has been developed to replace these Tc-99m-dependent agents.

MR imaging and clinical application of contrast media. Clinical magnetic resonance imaging (MRI) generates high-resolution images of the body through the acquisition of proton ($^1$H) nuclear magnetic resonance (NMR) signals from water and macromolecules in tissue. For "$T_1$-weighted" MR images, signal intensity increases in regions where longitudinal relaxation rate (spin lattice relaxation rate, $1/T_1$) increases. With "$T_2$-weighted" MRI, signal intensity decreases when transverse relaxation rate (spin-spin relaxation rate, $1/T_2$) increases. Both $T_1$ and $T_2$ weighted images are routinely acquired in virtually all clinical MRI studies.

Intravenous contrast agents are routinely administered in MRI to further increase $1/T_1$ or $1/T_2$, in an effort to better delineate diseased tissue from normal tissue, improve anatomical definition, and enhance characterization of physiological or pathological function. Almost all currently approved MRI contrast agents are based on chelates of the lanthanide metal Gd, with a small subset of angiographic and perfusion studies conducted using iron-oxide materials (e.g., Feraheme) off-label in patients with renal insufficiency/failure. Commercial Gd-based materials are used most commonly to increase $1/T_1$ in diseased tissue, where contrast material is prone to accumulate.

For tissue perfusion determinations with MRI, Gd-based agents or iron-oxide nanoparticles may be used, with acquisition strategies based on either $1/T_1$ or $1/T_2$ contrast, although $1/T_2$ contrast approaches are increasingly favored. Perfusion imaging is currently used clinically to characterize tumor aggressiveness, tumor response to therapy, and tissue viability in heart, brain and other organs.

Without wishing to be bound by theory, the mechanism of ascorbate signal change without paramagnetism, which is also described as "$T_2$-weighted contrast," is based on enhancement of the water proton ($^1$H) spin-spin relaxation rate $1/T_2$ (or reciprocally, spin-spin relaxation time, $T_2$), as solvent water protons are exchanged with hydroxyl protons on ascorbate molecules. The effect of proton exchange on $T_2$ contrast is amplified further by the dismutation reaction of the ascorbate radical at physiological pH. Ascorbate oxidation and ascorbate radical dismutation are, in turn, driven by the co-presence of oxidizing substrates such as hydrogen peroxide ($H_2O_2$) and/or hydrogen ("proton") exchange catalysts.

Ascorbate transport and excretion. Ascorbic acid is absorbed in the body by both active transport and simple diffusion. The two major active transport pathways are sodium-ascorbate co-transporters (SVCTs) and hexose transporters (GLUTs). SVCT1 and SVCT2 import the reduced form of ascorbate across the plasma membrane (Savini I, Rossi A, Pierro C, Avigliano L, Catani M V (April 2008). "SVCT1 and SVCT2: key proteins for vitamin C uptake". Amino Acids 34 (3): 347-55), whereas GLUT1 and GLUT3 glucose transporters transfer the oxidized form, dehydroascorbic acid (Rumsey S C, Kwon O, Xu G W, Burant C F, Simpson I, Levine M (July 1997). "Glucose transporter isoforms GLUT1 and GLUT3 transport dehydroascorbic acid". *J. Biol. Chem.* 272 (30): 18982-9). Although dehydroascorbic acid concentrations are low in plasma under normal conditions, the oxidized molecule is absorbed at much higher rates across GLUT1 and GLUT3 than the reduced form is across the SVCTs. When ascorbate concentrations are pharmacologically elevated, dehydroascorbate concentration also increases, enabling marked absorption where GLUT transporters exist in high copy such as in the brain (and blood brain barrier) and tumor cells. Once transported, dehydroascorbic acid is rapidly reduced back to ascorbate.

Ascorbate concentrations over the renal re-absorption threshold pass freely into the urine and are excreted with a half-life of about 30 minutes. At high dietary doses (corresponding to several hundred mg/day in humans) the renal resorption threshold is 1.5 mg/dL in men and 1.3 mg/dL in women (Oreopoulos D G, Lindeman R D, VanderJagt D J, Tzamaloukas A H, Bhagavan H N, Garry P J (October 1993). "Renal excretion of ascorbic acid: effect of age and sex". *J Am Coll Nutr.* 12 (5): 537-42). Ascorbate that is not directly excreted in the urine or destroyed by other body metabolism is oxidized by L-ascorbate oxidase and removed.

Ascorbate is understood to have a pharmacokinetic profile that resembles vancomycin. Biodistribution of oral ascorbate is under tight control, with plasma concentrations rarely exceeding 200 µM even at oral doses more than 100 times the recommended daily allowance (Levine M, Conry-Cantilena C, Wang Y, Welch R W, Washko P W, Dhariwal K R, Park J B, Lazarev A, Graumlich J F, King J, Cantilena L R (April 1996). "Vitamin C pharmacokinetics in healthy volunteers: evidence for a recommended dietary allowance". Proc. Natl. Acad. Sci. USA 93 (8): 3704-9). Ascorbate administered intravenously, however, bypasses these tight control systems, with plasma concentrations of 10 mM or higher achievable. Plasma concentrations higher than 10 mM are safely sustained in humans for up to 4 hours with remarkably low toxicity (Hoffer L J., Levine M., Assouline S., Melnychuk D., Padayatty S J., Rosadiuk K., Rousseau C., Robitaille L., and Miller W H., Jr., Phase I clinical trial of i.v. ascorbic acid in advanced malignancy. Ann Oncol 19: 1969-1974, 2008).

The present invention is explained in greater detail in the following non-limiting examples.

In Vitro Examples

Ascorbate Enhancement of Spin-Spin Relaxation Rate, $1/T_2$

Previous studies have reported on the NMR/MRI contrast effects on $T_2$-weighting arising from exchange of bulk water protons with mobile protons of low molecular weight solutes and macromolecules (e.g., $-NH_2$, $-OH$, $-SH$, $-NH$). The contrast effect on $1/T_2$ from this proton exchange is described as follows:

$$\frac{1}{T_2} = \frac{1}{T_{2a}} + f_{CR}(P_b, \delta\omega_b, k, T_{2b}, \tau)$$

Bulk water is related to $_a$ and exchangeable protons (e.g., from an ascorbate OH group) to $_b$. $f_{CR}$ is a Closed Function with Five Parameters, Derived from Carver and Richards and Refined by Hill et al. (Carver, J. P.; Richards, R. E. J. General 2-Site Solution For Chemical Exchange Produced Dependence Of T2 Upon Carr-Purcell Pulse Separation J. Magn. Reson. 1972, 6, 89-105; Hills, B. P.; Wright, K. M.; Belton, P. S. N.M.R. studies of water proton relaxation in Sephadex bead suspensions Mol. Phys. 1989, 67, 1309-1326). For the hydroxyl protons of ascorbate, Pb would be the fraction of exchangeable protons, k is the exchange rate between exchangeable protons and water protons, stub is the chemical shift between hydroxyl and bulk water protons, and $T_{2b}$ is the local spin-spin relaxation time of hydroxyl protons. T is the inter-pulse (90°-180°) spacing in the $T_2$-weighted acquisition sequence.

An essential but often neglected parameter influencing proton exchange on $T_2$ contrast is the role of exchange catalysis (Liepinsh E and Otting, G Proton exchange rates from amino acid side chains—implications for image contrast. Magn Reson Med. 1996 35(1): 30-42). The rate constant k for proton exchange between OH or NH groups and water can be described by $$k = k_a[H^+] + k_b[OH^-] + \Sigma k_c[\text{catalyst}]^y$$

$K_a$, $K_b$ and $K_c$ denote the exchange rate constants due to catalysis by $H^+$, $OH^-$ and other exchange catalysts, respectively. The exponent y is 1 or 2 depending on the mechanism of a given exchange catalyst. The rate constants $K_a$ and $K_b$ can be calculated in turn by:

$$k_{a,b} = k_D \frac{1}{1 + 10^{pKD-pKA}}$$

where $K_D$ is the rate constant for diffusion controlled encounter of the proton donor and acceptor (~$10^{10}$ mol$^{-1}$s$^{-1}$), and $pK_D$ and $pK_A$ are the pK values of the proton donor and acceptor. Although $pK_{H3O+}$ and $pK_{OH-}$=15.7, $K_c$ is more challenging to predict because of the nonlinear dependence of proton transfer on catalyst concentration. Nonetheless, efficient exchange catalysis at neutral pH is attained with at least a moderate difference between $pK_D$-$pK_A$ and a significant concentration of catalytically active acidic or basic forms of the exchange catalysts at physiological pH.

Thus $H_2O$, despite its high concentration, is a relatively poor proton donor and therefore an inefficient exchange catalyst at physiological pH because the $pK_A$ of the primary species ($H_3O^+$ and $OH^-$) is 15.7. On the other hand, recognized exchange catalysts in physiological conditions include organic phosphates, carbonates (e.g., bicarbonate, $HCO_3^-$), and molecules with carboxyl and amino groups (Liepinsh E and Otting, G Proton exchange rates from amino acid side chains—implications for image contrast. Magn Reson Med. 1996, 35(1): 30-42).

As shown below, another powerful catalyst not previously recognized is ascorbate, which possesses one hydroxyl group having a favorable $pK_A$=6.75 at the 4 position, as well as an equilibrium disproportionation reaction with a $pK_A$=7.0. Thus, ascorbate has the potential to not only 'self-catalyze' but also to be an efficient catalyst of proton exchange for basic hydroxyl groups on sugars and other macromolecules.

Figure 2:
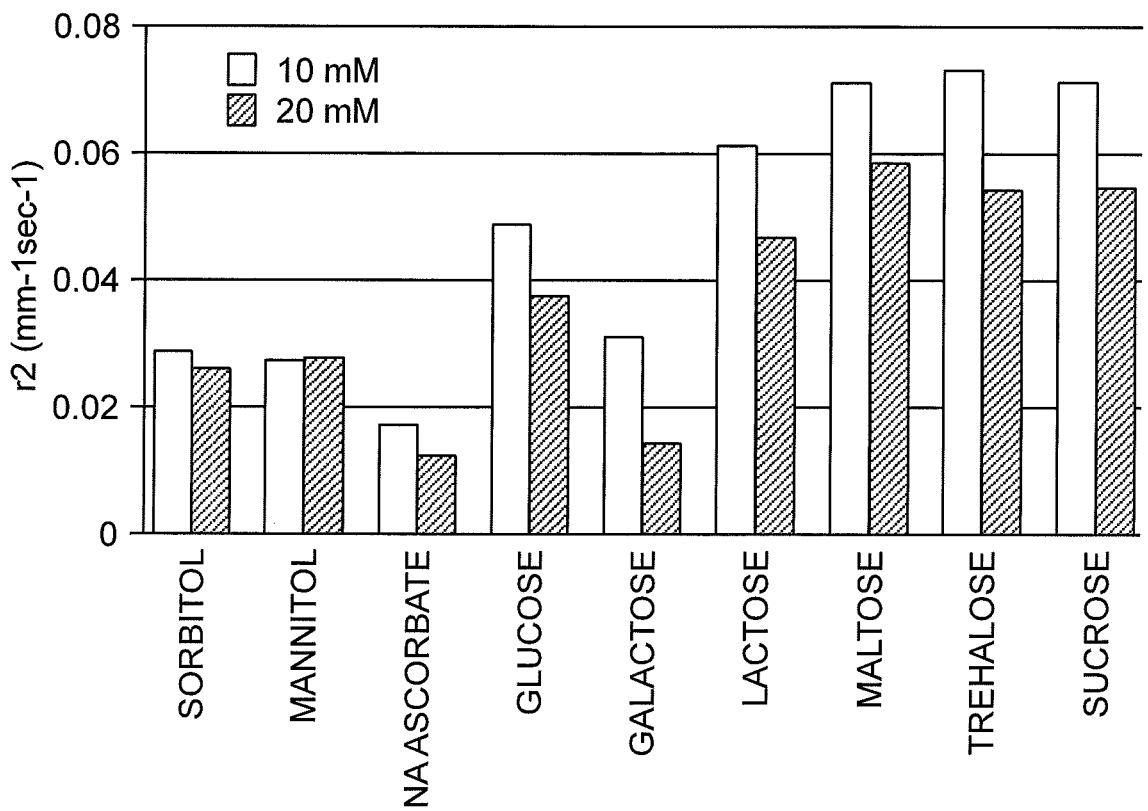
FIG. 2. $T_2$ relaxivity (r2=mM$^{-1}$sec$^{-1}$) of sugars, sugar alcohols, and ascorbate Comparisons include both mono and disaccharides. As discussed in the text, note the diminishing contrast effect at higher concentration, which is believed to be secondary to self-association of like moieties and reduced proton exchange.

FIG. 2 shows a comparison on $T_2$ enhancement of pure solutions of several sugars, sugar alcohols, and ascorbate in deionized water at pH 7. Data are provided from quantitative $T_2$ mapping at 7T using a RARE FSE protocol with at least 6 different echo times, at solute concentrations of 10 and 20 mM. As shown, $T_2$ relaxivity is roughly a function of the number of exchangeable OH protons available on each molecule, with disaccharides, as predicted, producing proportionally greater contrast effect than monosaccharides. Noteworthy is the nonlinear dependence on solute concentration, with relaxivity enhancement decreasing as concentration is increased, a phenomenon that is likely related to self-association of sugars in pure solutions. The latter is particularly relevant to observations described below, where overall $T_2$ effects are instead synergistically enhanced when ascorbate and sugars are combined together at higher total solute concentrations. Formulations combining ascorbate with mono or disaccharides provide a means to deliver higher concentrations of both species in order to increase $T_2$ contrast effects for MR imaging.

Figure 3A:
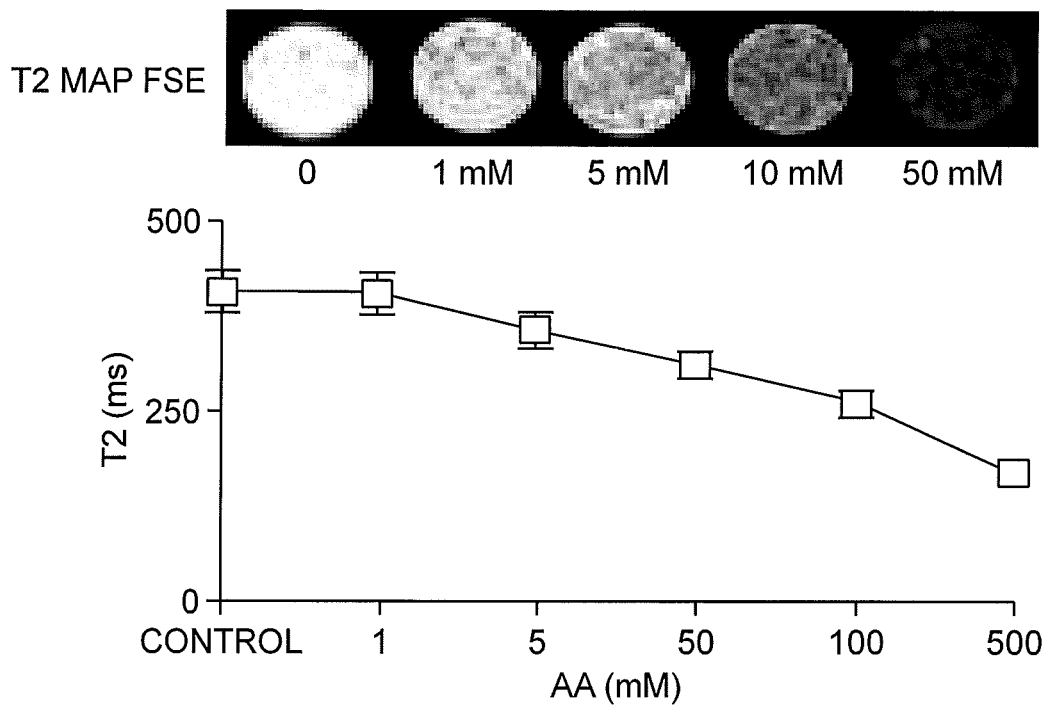
FIGS. 3A-3D. In vitro ("phantom") experiments on ascorbate spin-spin relaxation ($T_2$-weighted) MRI contrast.
Figure 3B:
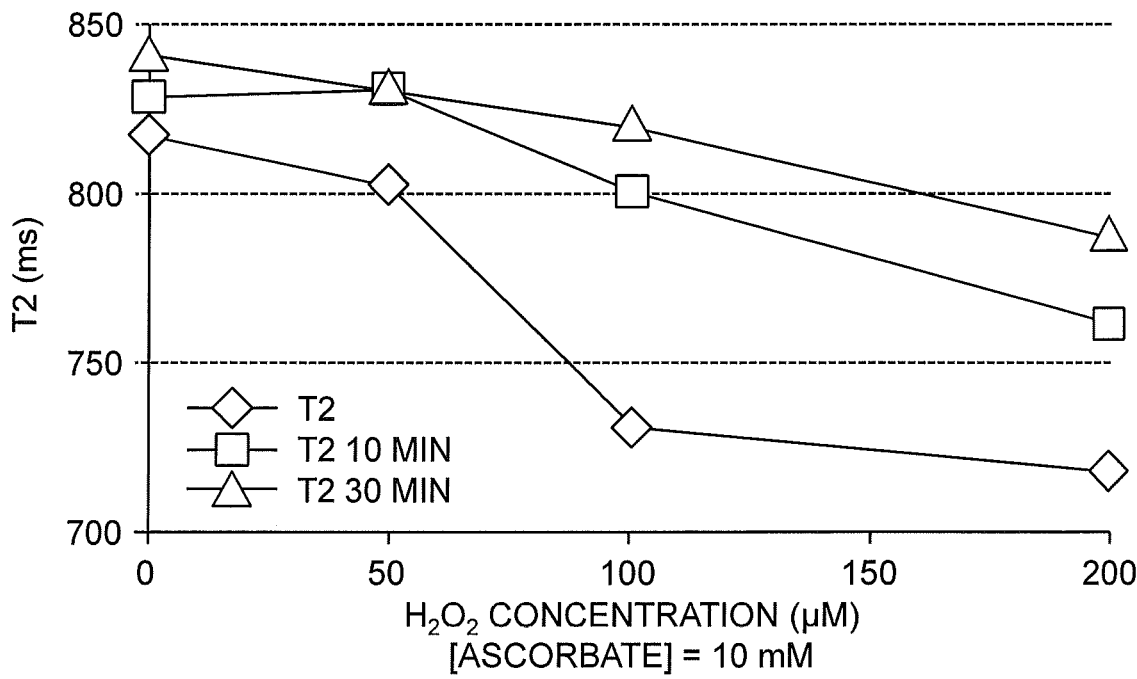
Figure 3C:
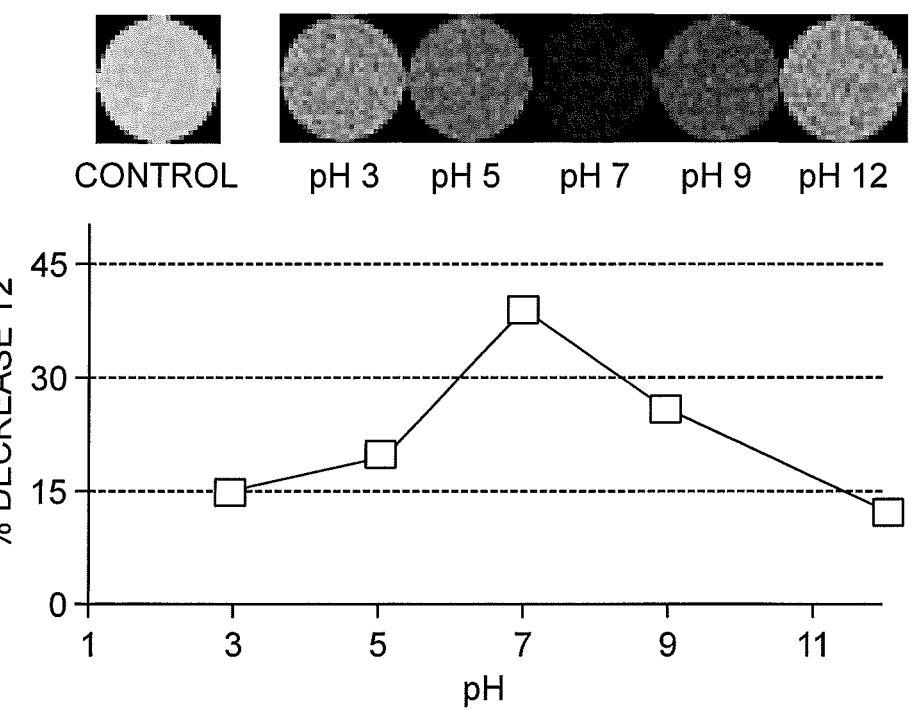

FIG. 3A depicts a more detailed demonstration of $T_2$ effects of pure ascorbate solutions at different concentrations at neutral pH. FIG. 3B reveals the marked enhancement of the $T_2$ effect when ascorbate is in the presence of only µM (i.e., physiological) concentrations of hydrogen peroxide ($H_2O_2$), which drives oxidation to dehydroascorbate as well as ascorbate radical dismutation. Although $H_2O_2$ is also considered an exchange catalyst in its own right, the dramatic effect observed on ascorbate-mediated $1/T_2$ enhancement when $H_2O_2$ is present at 100-fold less concentration than ascorbate suggests that proton exchange from $H_2O_2$-driven ascorbate oxidation/dismutation, rather than direct exchange from OH ascorbyl protons, is an important contributory mechanism responsible for $T_2$ changes. Further evidence of the contribution from dehydroascorbate oxidation/dismutation on proton exchange is depicted in FIG. 3C showing that the $1/T_2$ enhancement effect is by far the most significant at neutral pH where the reaction rate of ascrobate-dehydroascorbate dispropotination is also greatest.

Figure 3D:
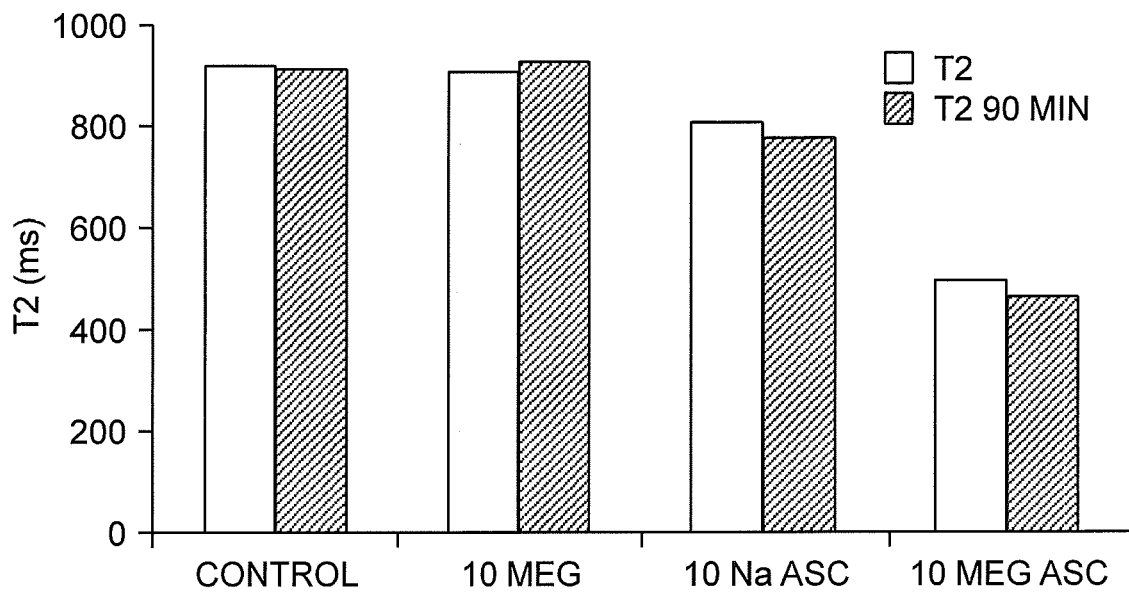

Data in FIG. 3D provide the first suggestion that exchange catalysis between ascorbate and an acceptor/donor molecule with an appropriate pK can markedly drive $1/T_2$ enhancement change. Data here compare solutions of ascorbate (10 mM) as sodium salt and as meglumine (aminosugar) salt. Here the $T_2$ contrast effect ($T_2$ relaxation in ms) is approximately 4 times greater with meglumine ascorbate as compared to either meglumine or ascorbate alone in water at neutral pH.

Figure 4:
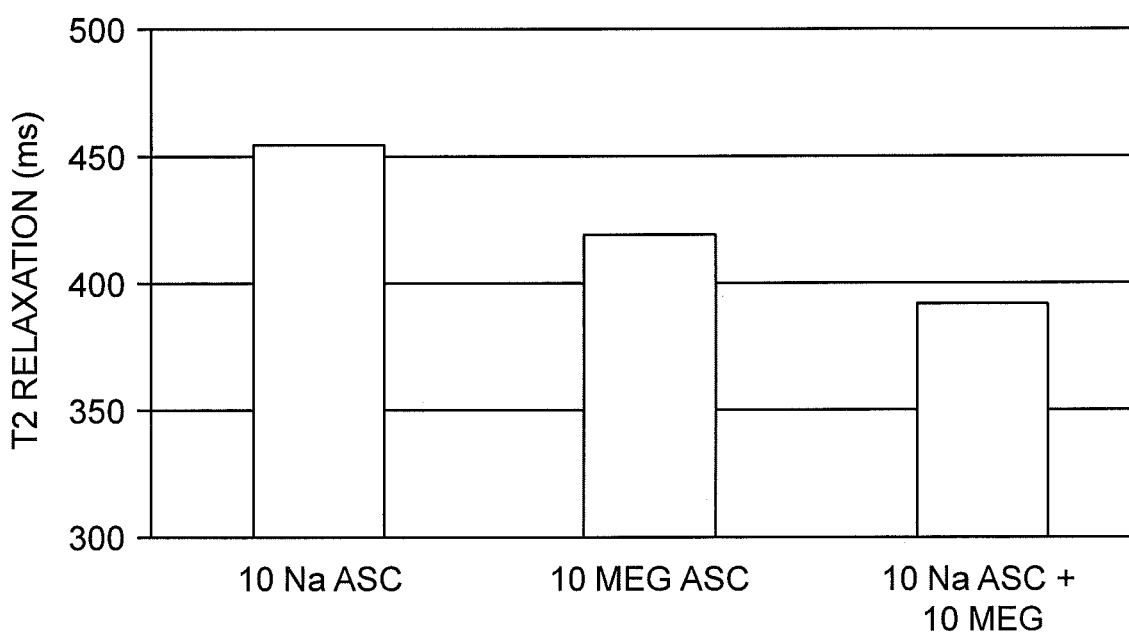
FIG. 4. Comparison of Ascorbate as Na or Meglumine (MEG) Salt. Solutions are prepared with physiological concentrations of $PO_4$ (2 mM) and $HCO_3^-$ (25 mM) buffers.

It was subsequently investigated whether the impressive synergistic effect of meglumine with ascorbate was dependent on chemical association with ascorbate as a salting cation (even though in theory the two moieties should be fully dissociated in water). FIG. 4 reveals that proton exchange is actually synergized when the 'salting function' is performed by $Na^+$ cations, presumably leaving the amine group in addition to the basic OH groups of meglumine to participate in exchange catalysis with ascorbate. Note that here control $T_2$ relaxation (ms) values ($T_2$=840 ms) are not shown to better illustrate differences between experimental groups.

Figure 5:
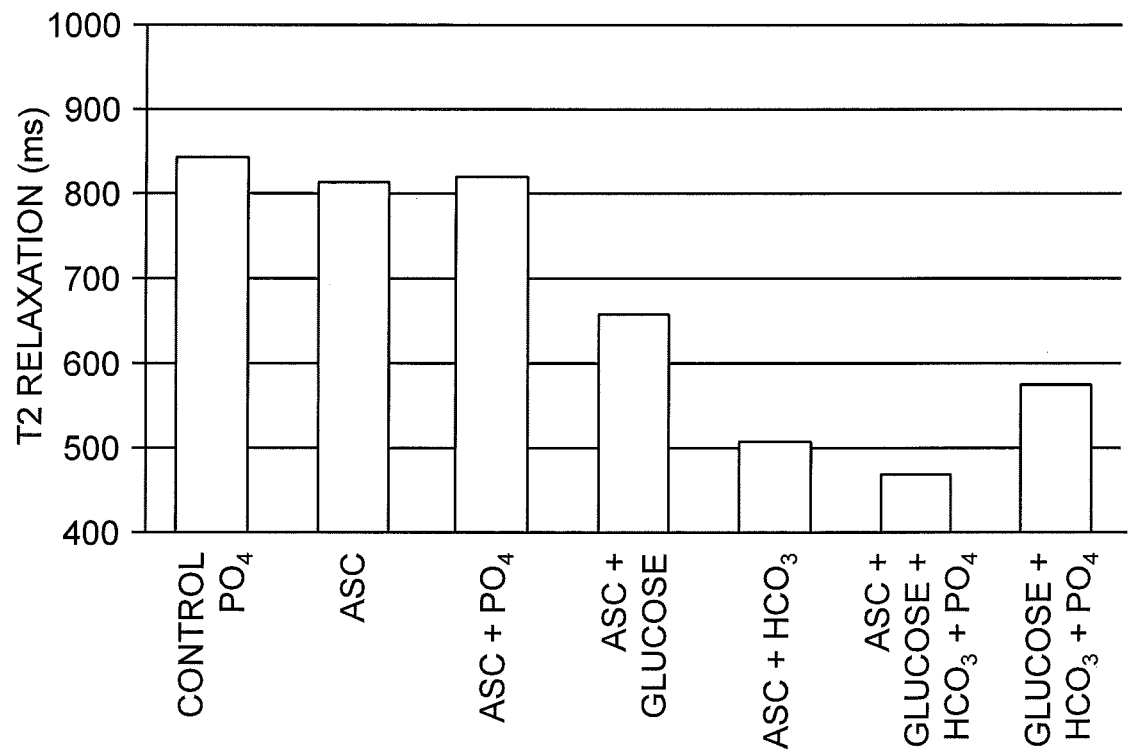
FIG. 5. Na Ascorbate (Asc)+Physiological Exchange Catalysts. Each solution is set at neutral (pH=7.0) in deionized water. Concentrations of physiological exchange catalysts are the same as the in vivo in serum and extracellular space: $PO_4$=2 mM, glucose=5 mM, and $HCO_3^-$ is 25 mM.

FIG. 5 summarizes $T_2$ relaxation data from a series of experiments looking at the influence of various physiological exchange catalysts on the contrast effect from ascorbate. Using known serum and extracellular concentrations of $PO_4$=2 mM, glucose=5 mM, and $HCO_3^-$ of 25 mM, with ascorbate at 10 mM, $T_2$ relaxation of each of these moieties was examined individually and in combination. As shown, the $T_2$ relaxation effect of ascorbate alone or with $PO_4$ in water is modest but in the presence of physiological concentrations of either glucose or $HCO_3^-$ is dramatically increased, with 10 mM ascorbate, (a plasma concentration easily and safely achieved with parenteral administration) producing a remarkable 50% change in $T_2$ relaxation. The greatest enhancement is seen with ascorbate in the presence of glucose, $HCO_3^-$, and $PO_4$ together at known concentrations in vivo. Thus, by simply administering ascorbate i.v., the $T_2$ enhancement effect of ascorbate in vivo will be much greater than what might be expected after only looking at ascorbate alone in phantom studies without physiological exchange catalysts present.

Figure 6:
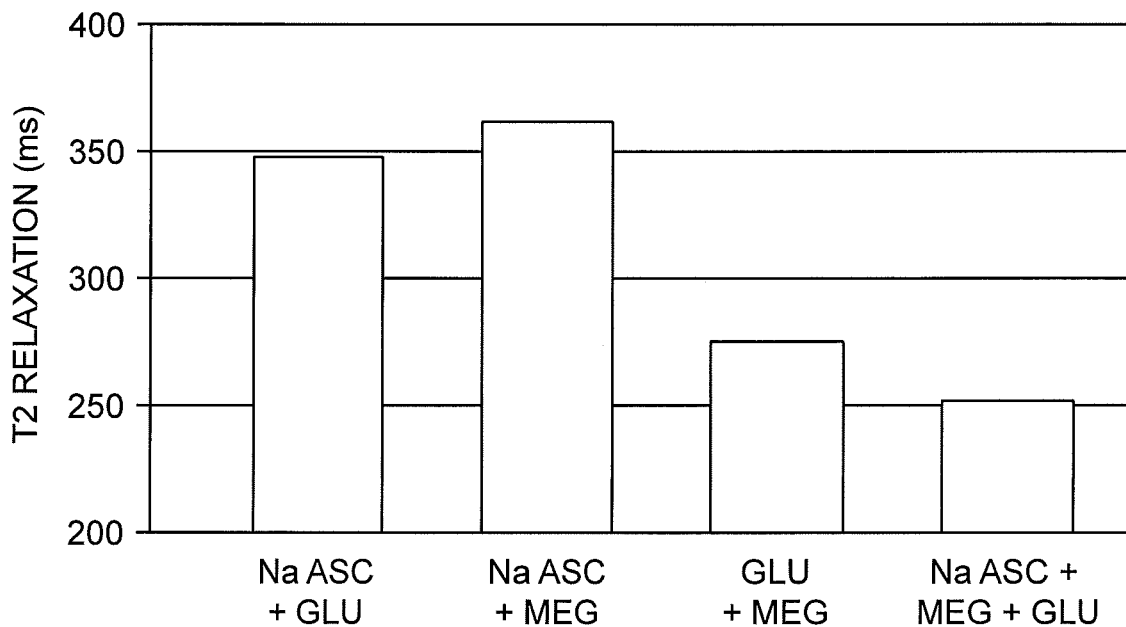
FIG. 6. Exchange Synergism Between Na Ascorbate (Asc)/Meglumine (Meg) and Glucose (Glu). Solutions are compared in the setting of physiological buffers $PO_4$ (2 mM) and $HCO_3^-$ (25 mM) that also contribute as exchange catalysts.

Also predicted from the experiments above is the possibility that formulation of ascorbate with other sugars that are not normally present in vivo may further catalyze the ascorbate contrast effect. FIG. 6, for example, demonstrates additional synergism when meglumine is added to a solution of sodium ascorbate at equivalent concentration (20 mM) and into a background of 2 mM $PO_4$, 25 mM $HCO_3^-$. Data show comparison with or without physiological concentrations (5 mM) of glucose, as well as the effect of meglumine alone added to the physiological catalysts. As seen the greatest contrast effect is observed when all moieties are combined. One implication therefore is that higher contrast effects may be achievable by combining different exchange catalysts with each other, thus limiting the concentration of any one exogenously administered species.

Figure 7:
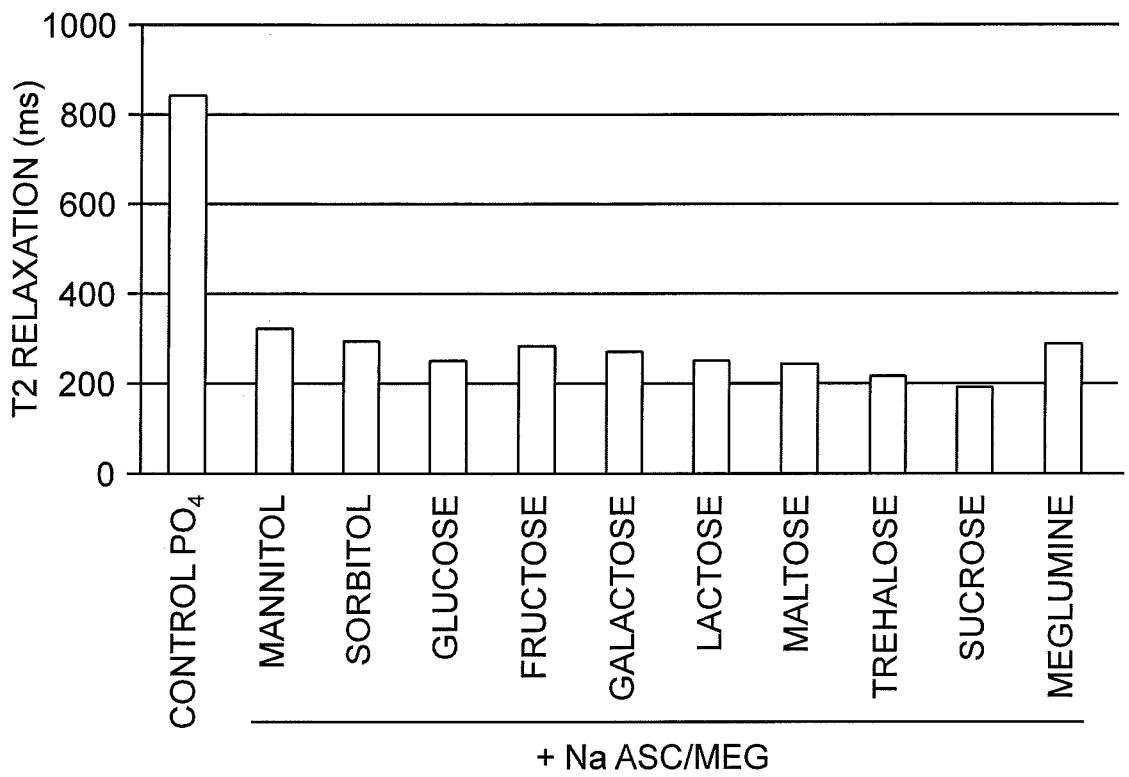
FIG. 7. Exchange synergism of Na Asc/Meglumine (Meg) with sugar alcohols, mono- and disaccharides. All solutions are prepared in co-presence of 2 mM $PO_4$ and 25 mM $HCO_3^-$.
Figure 8:
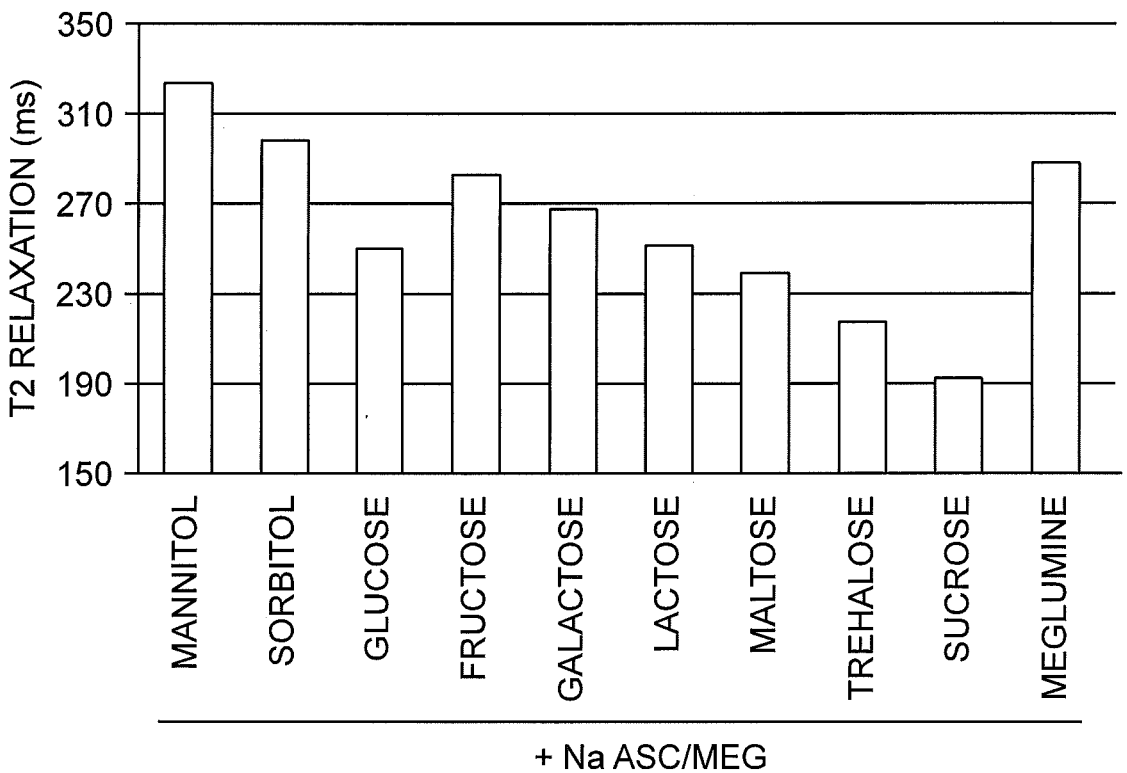
FIG. 8. Rescaled data without control for exchange synergism of Na Asc/Meglumine (Meg) with sugar alcohols, mono- and disaccharides. All solutions are prepared with 2 mM $PO_4$ and 25 mM $HCO_3^-$.

FIG. 7 summarizes data extending this concept, testing potential synergisms when Na ascorbate and meglumine are formulated with other mono and disaccharides and sugar alcohols. As shown the contrast effects are dramatic with each potential formulation. In FIG. 8, the control solution (2 mM $PO_4$ and 25 mM $HCO_3^-$) to better illustrate the differences in contrast changes between groups. The strongest effect thus observed is when ascorbate and meglumine are combined with the common disaccharide sucrose, thus suggesting a promising candidate formulation (i.e., ascorbate/ meglumine/sucrose) for MRI using only moieties that may all be safely administered parenterally.

In Vivo Example 1

Normal Brain Perfusion and Metabolic Change

Figure 9A:
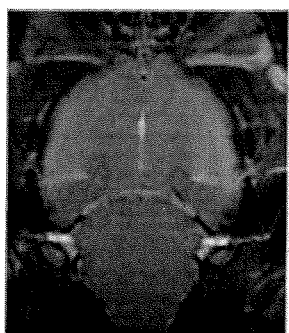
FIGS. 9A-9B. In vivo ascorbate $T_2$ contrast changes following high dose parenteral ascorbate (2 g/kg, right IJ i.v. injection).
Figure 9A:
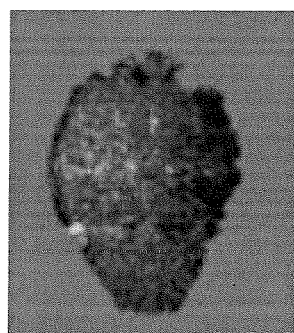
Figure 9A:
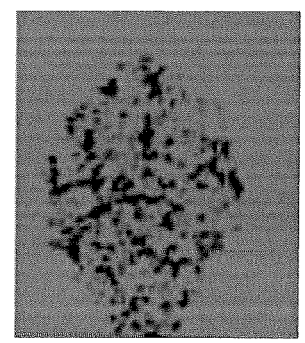
Figure 9B:
Figure 9B:
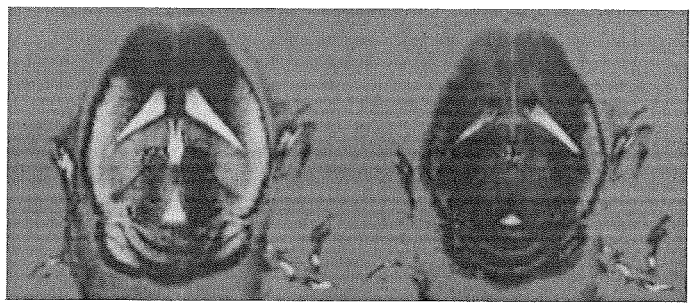
Figure 9B:
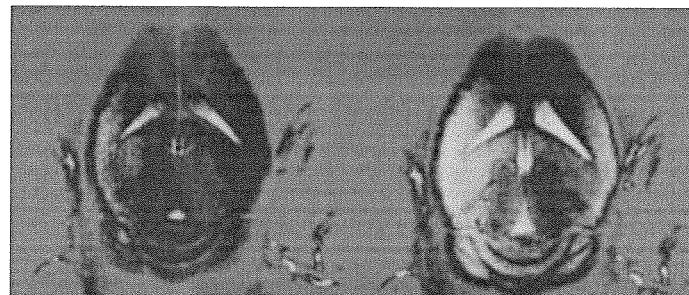

In vivo ascorbate $T_2$ contrast changes were determined following high dose parenteral ascorbate (2 g/kg, right IJ i.v. injection.) FIG. 9A, shows a conventional single slice axial FSE T2WI image through the midbrain of a normal C57 black mouse, and the two images on the right demonstrate a 'first pass' extraction of contrast change during and following ascorbate administration i.v. T2 signal in brain tissue immediately following, and 10 minutes after, ascorbate administration is acquired and then subtracted from the T2 brain signal acquisition pre-ascorbate administration. Since ascorbate produces a decrease in signal intensity, subtraction from the higher signal pre-dose scan results in a net positive 'map' of flow-through perfusion (blood flow) through brain tissue. At 10 minutes, the perfusion effect has nearly resolved and early signal intensity changes related to tissue uptake are beginning to be observed. FIG. 9B, show the signal changes due to tissue uptake of high-dose ascorbate. Color-lute maps of signal intensity are not subtracted from the pre-dose scan and therefore show the expected decreases in T2 signal over time, maximized between 30-60 min in normal C57 mice.

In Vivo Example 2

Figure 10:
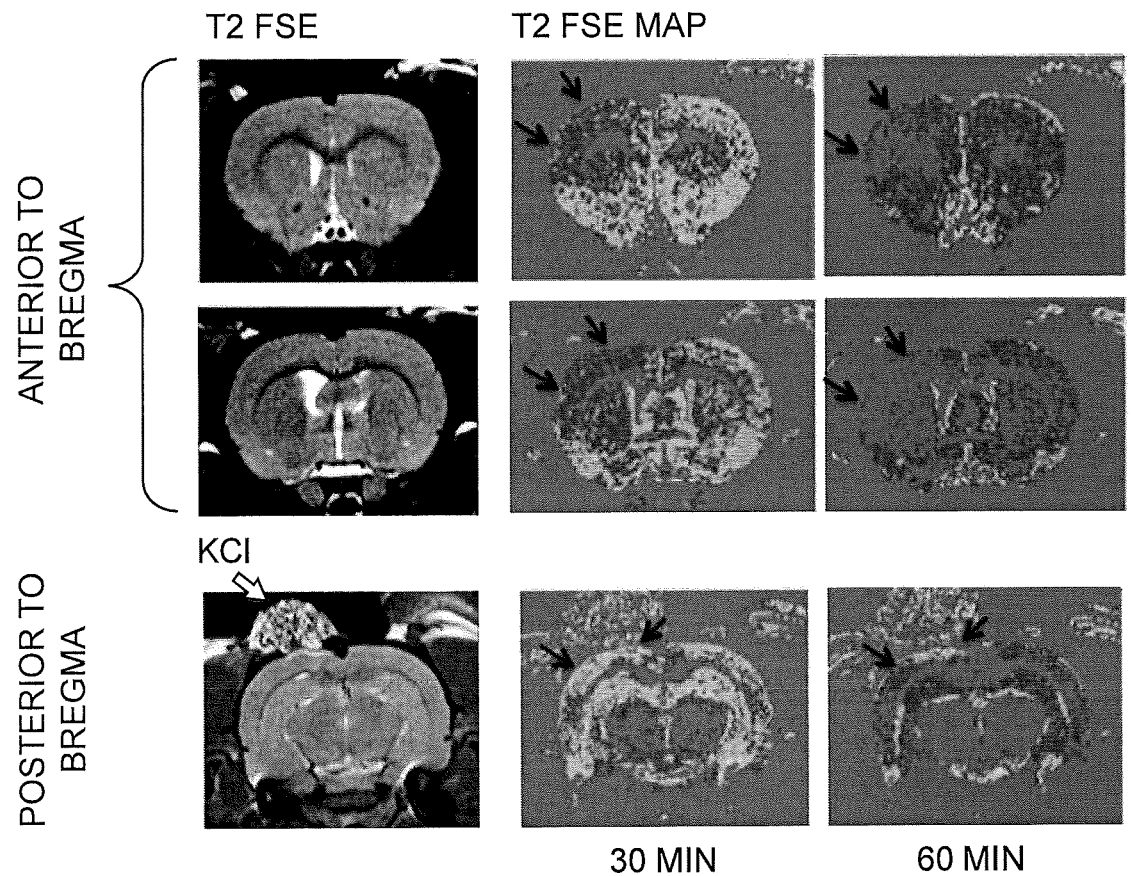
FIG. 10. Ascorbate T2 enhancement in a rodent model of neocortical spreading depression (SD). In the illustrated experiment, the lower row of images shows a tiny craniectomy with gelfoam (red arrow) soaked in a high concentration of potassium chloride (KCl), which diffuses locally into the adjacent parietal cortex. The craniectomy site is 1 mm posterior to bregma, a skull landmark representing the posterior third of the underlying brain. The above two rows show T2 images and quantitative color lute T2 maps of signal change in rodent brain that are 3 and 4 mm anterior to bregma, that is, distant from the SD induction site. T2 signal changes in the anterior slices demonstrate clear T2 asymmetry in the right cerebral cortex as compared to the left (again, SD remains confined to the right hemisphere). These marked cortical signal changes are consistent with the known hypermetabolic activity that occurs with SD, as also observed with $^{18}$F-FDG PET, and with direct microdialysis and metabolomic determinations. Of note, the opposite observation (focally increased T2 signal) is seen directly under the craniectomy site itself (row three), consistent with localized edema (increased free water) at the site of KCl infusion.

Focal Cerebral Hypermetabolism in Association with Neocortical Spreading Depression FIG. 10 shows ascorbate T2 enhancement in a rodent model of neocortical spreading depression. Spreading depression (SD) is an experimentally reproducible pathophysiological phenomenon of CNS tissues originally described 60 years ago by Loao. After a focal region of cortex reaches a critical threshold of ionic perturbation, a massive spreading wave of cellular depolarization may begin and spread through gray matter tissue, but remain confined to the gray matter zone in which it was induced, not crossing white matter pathways. If the induction mechanism (e.g., a local high concentration of applied potassium chloride) is continuous to the same region, these waves of SD will recur once every 8-10 minutes and last over a 2-3 hour period. Marked changes in brain metabolism accompany SD, and, since no histologically detectable neuronal injury is present after SD, these metabolic changes parallel metabolic fluxes in non-ischemic, hyperexcitable brain tissue such as epileptogenic foci.

In the above experiment, the lower row of images shows a tiny craniectomy with gelfoam (red arrow) soaked in a high concentration of KCl, which diffuses locally into the adjacent parietal cortex. The craniectomy site is 1 mm posterior to bregma, a skull landmark representing the posterior third of the underlying brain. The above two rows show T2 images and quantitiative color lute T2 maps of signal change in rodent brain that are 3 and 4 mm anterior to bregma, that is, distant from the SD induction site. T2 signal changes in the anterior slices demonstrate clear T2 asymmetry in the right cerebral cortex as compared to the left (again, SD remains confined to the right hemisphere). These marked cortical signal changes are consistent with the known hypermetabolic activity that occurs with SD, as also observed with $^{18}$F-FDG PET, and with direct microdialysis and metabolomic determinations. Of note, the opposite observation (focally increased T2 signal) is seen directly under the craniectomy site itself (row three), consistent with localized edema (increased free water) at the site of KCl infusion.

In Vivo Example 3

Cardiac Perfusion and Metabolic Imaging

Figure 11A:
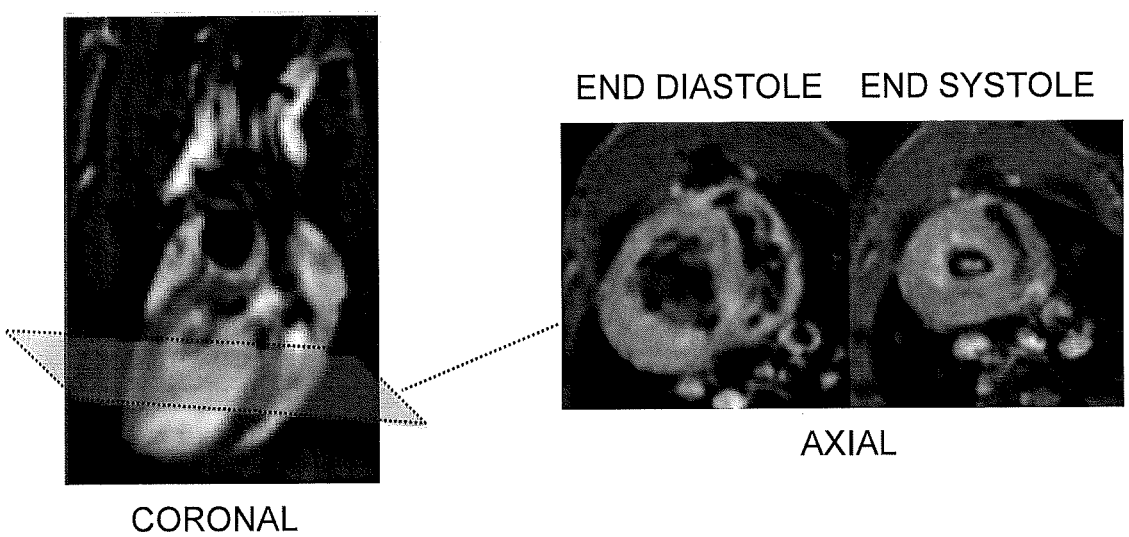
FIGS. 11A-11B. Perfusion and viability cardiac imaging with parenteral ascorbate.
Figure 11B:
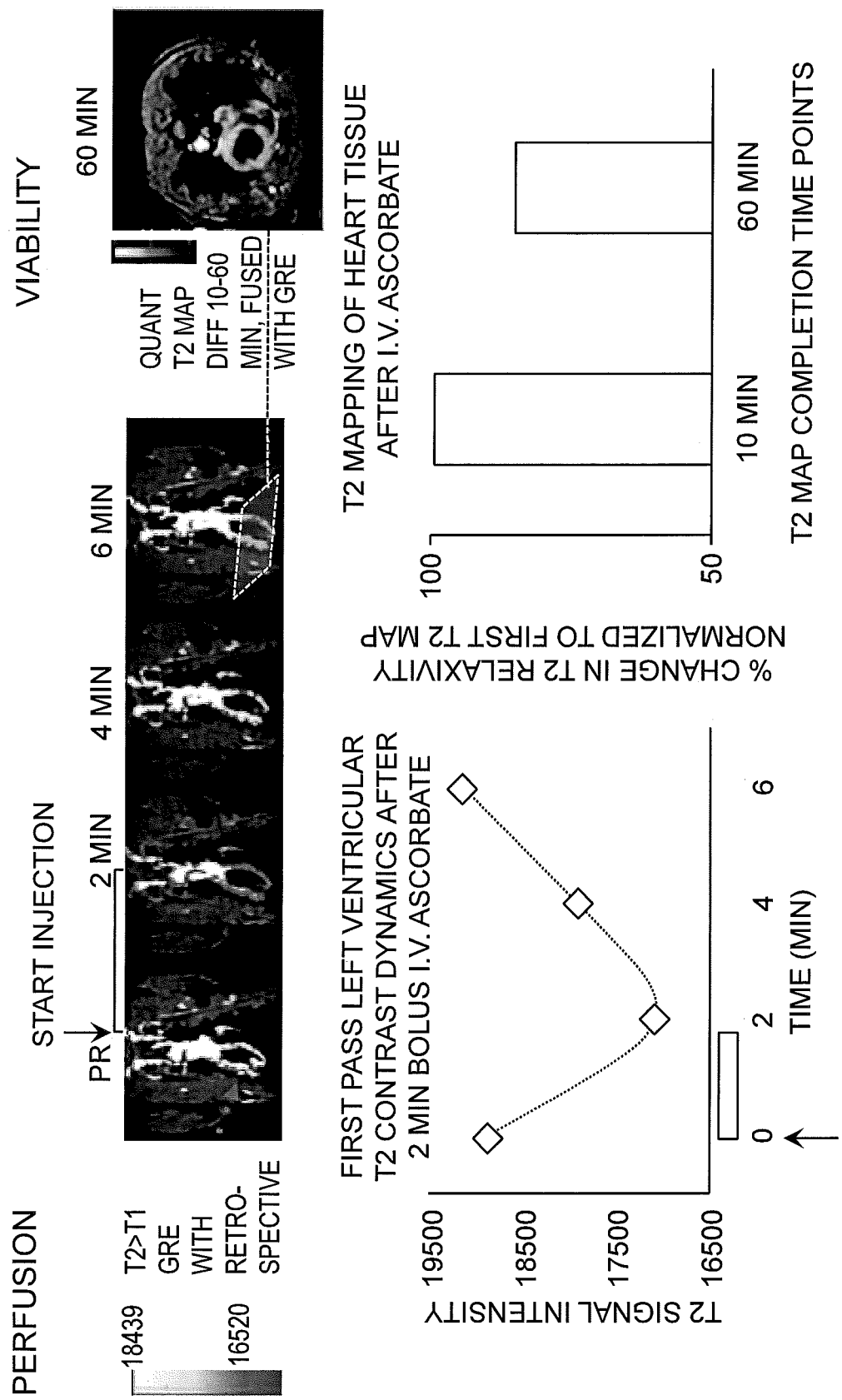

Perfusion and viability cardiac imaging with parenteral ascorbate was assessed. FIG. 11A, depicts the two primary imaging planes, coronal and axial, for rat heart imaging at 7T. Retrospective gating with respiratory coupling was employed to collect images at 7T. The acquisition sequence is moderately T2-weighted and can be further optimized to enhance the contrast effect. FIG. 11B, shows transient decrease in T2 signal intensity throughout the left ventricle with initial bolus of ascorbate injection i.v. After the initial bolus for first pass flow or 'perfusion imaging' quantitative T2 maps using variable flip angles show gradual T2 contrast change in heart tissue reflecting ascorbate uptake. Only viable, metabolically active cells will take up ascorbate.

share humans' inability to synthesize ascorbate endogenously, MRI effects in this model may be more predictive of MRI changes in patients. Ascorbate was administered parenterally via femoral or jugular vein access using controlled infusion for a total dose of 2 g/kg over 60 minutes. MRI was performed for 90 minutes.

Figure 12A:
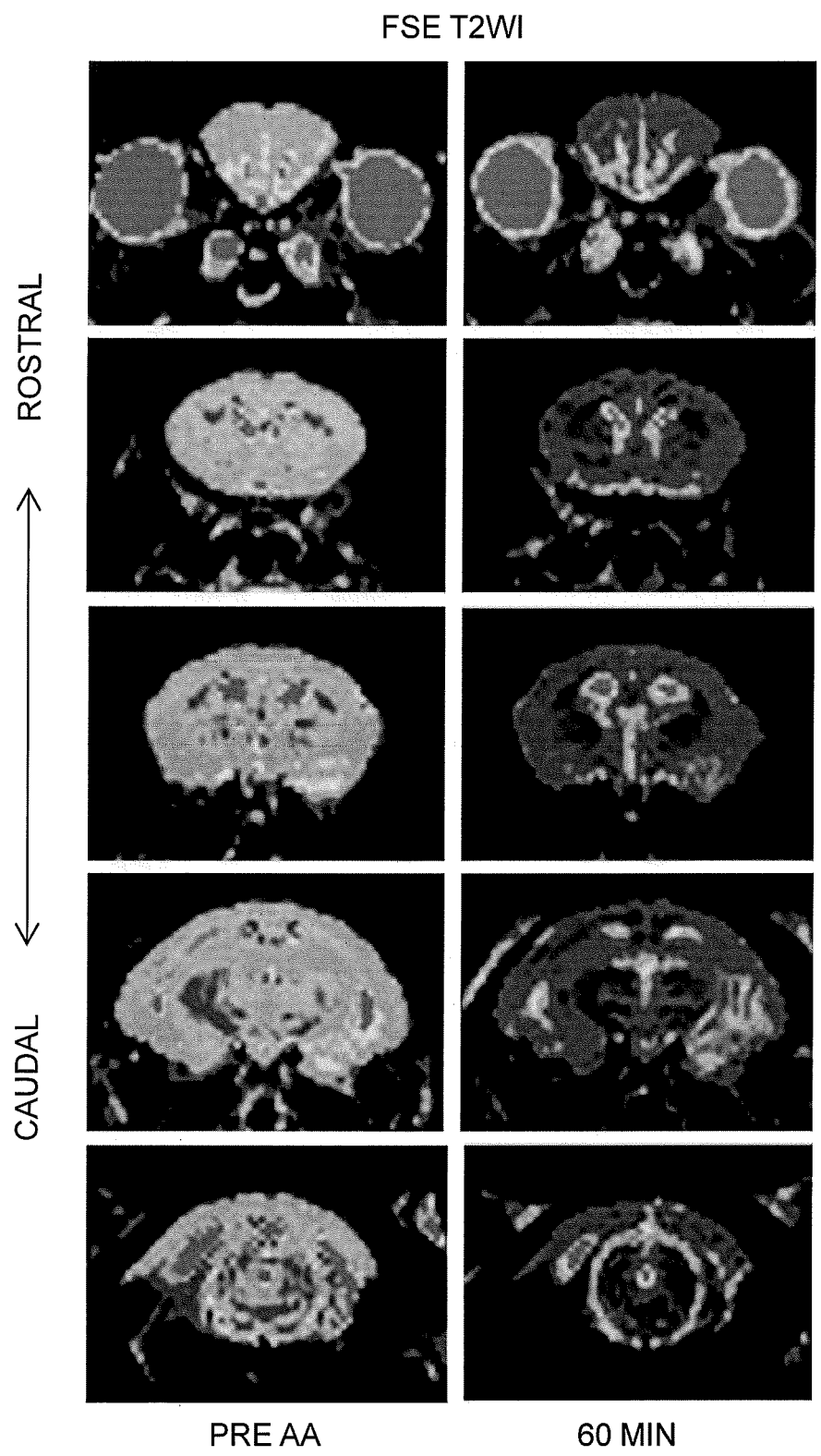
FIGS. 12A-12C. T2 contrast changes in guinea pigs following i.v. administration of three different formulations of ascorbate.

FIG. 12A shows Fast spin echo (FSE) T2 images before and after 60 min slow infusion of ascorbate show dramatic signal intensity differences throughout the brain parenchyma.

Figure 12B:
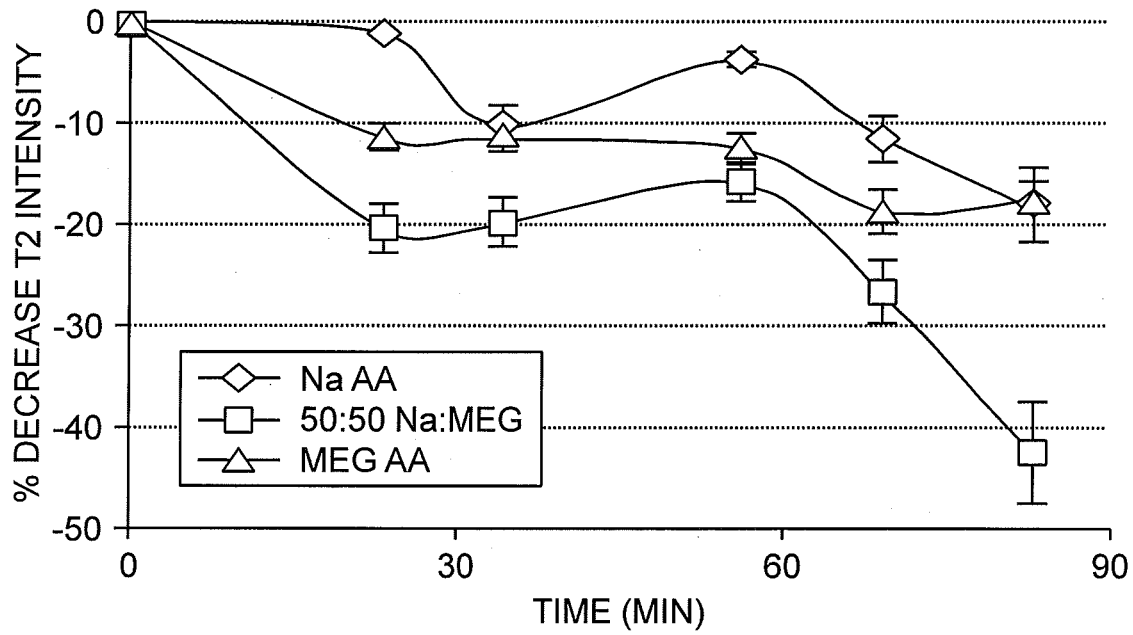
Figure 12C:
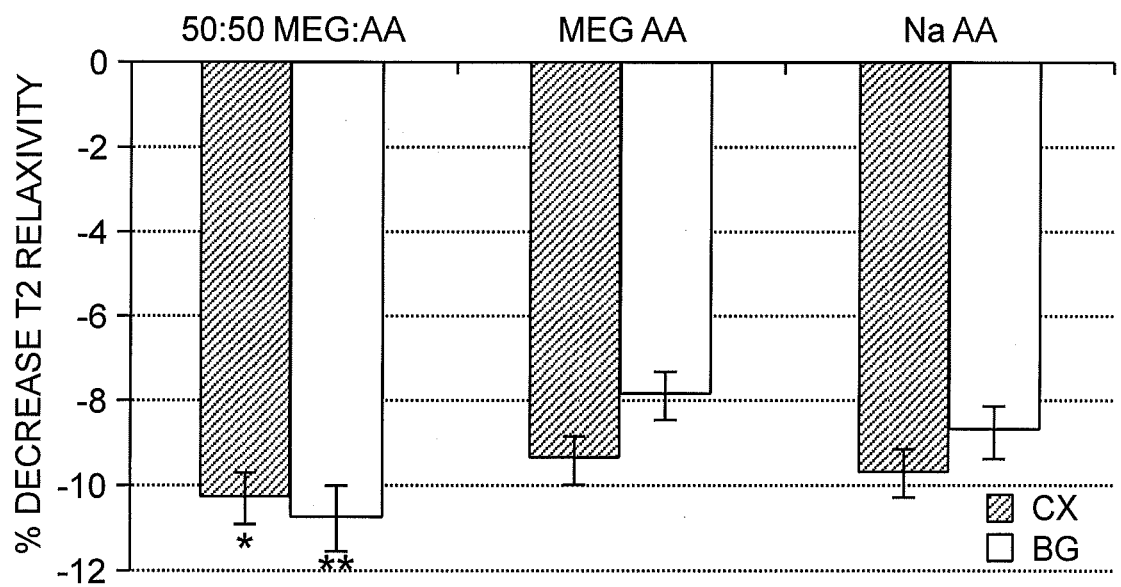

In FIG. 12B and FIG. 12C, normalized signal intensity changes and quantitative relaxivity measurements are shown for both guinea cerebral cortex (Cx) and basal ganglia (BG) after administration of three different ascorbate formulations: (1) 100% sodium ascorbate; (2) 50% sodium ascorbate and 50% meglumine ascorbate; and (3) 100% meglumine ascorbate. In FIG. 12B, signal intensity changes are greatest at each time point during and following administration of the second formulation (2) consisting of 50% Na AA: 50% Meg AA, with observed cortical FSE T2 intensity decreases exceeding 40%. Calculated T2 relaxivity values in FIG. 12C also show a greater than 10% from baseline with

TABLE 1

Example 4
Example parenteral formulations useful for MRI imaging

| | $T_2W$ contrast agent | Cation | Exchange catalyst | Osmolarity |
|---|---|---|---|---|
| I | ascorbate 100-600 mM | sodium 100-600 mM* | | 200-1200 mOsm/L |
| II | ascorbate 100-600 mM | meglumine 100-600 mM | meglumine 100-600 mM | 200-1200 mOsm/L |
| III | ascorbate 100-600 mM | sodium 250-300 mM; N-methyl-D-glucamine 250-300 mM | meglumine 100-300 mM | 200-1200 mOsm/L |
| IV | ascorbate 100-300 mM | sodium 100-300 mM | meglumine 100-300 mM | 200-1200 mOsm/L |
| V | ascorbate 100-300 mM | sodium 100-300 mM | reducing sugars 100-300 mM | 200-1400 mOsm/L |
| VI | ascorbate 100-300 mM | sodium 100-300 mM | non-reducing sugars 100-300 mM | 200-1400 mOsm/L |
| VII | non-reducing sugars[a] 0.1-1.0M | | meglumine 0.0-1.0M | 200-1400 mOsm/L |
| VIII | reducing sugars[b] 0.1-1.0M | | meglumine 0.0-1.0M | 200-1400 mOsm/L |

*sodium may be provided, e.g., as NaOH or $NaHCO_3$.
[a]non-reducing sugars include, e.g., sucrose, trehalose
[b]reducing sugars include, e.g., glucose, galactose, glyceradledyde, fructose, ribose, xylose, lactose, maltose Example 5

Example Preparation of Parenteral Formulation Useful for MRI Imaging

Formulation II above is prepared in the following manner: Into 500 mL sterile water are added 50 g of ascorbic acid (568 mM) and 55.4 g N-methyl-D-glucamine (568 mM). Stir until solution clears. mOsm/L~1100. pH~7.0. To promote long-term stability, add 0.025% EDTA disodium, prepare in de-oxygenated solution under nitrogen blanket and under light-sensitive conditions.

In Vivo Example 6

T2 Contrast Changes in Guinea Pigs Following Intravenous Administration of Three Different Formulations of Ascorbate We examined T2 contrast changes in whole brains of lightly anesthetized guinea pigs at 7T. Since guinea pigs formulation (2), with maximal values statistically greater than either formulation (1) or (3). On conventional FSE T2 weighted images, signal intensity changes with Meg AA (3) are also noted to be greater than those observed with sodium ascorbate (1) at nearly every time point, however T2 relaxivity calculations do not show statistical differences between these latter two formulations.

The foregoing is illustrative of the present invention, and is not to be construed as limiting thereof. The invention is defined by the following claims, with equivalents of the claims to be included therein.

That which is claimed is:

1. A method of enhancing a magnetic resonance imaging (MRI) image of a body or body region, or an organ or organ region in a subject, comprising:

parenterally administering to said subject in an MRI image-enhancing amount a sterile aqueous composition comprising:

100-600 mM ascorbate; and
100-600 mM sodium, meglumine, or a combination thereof,
wherein said composition comprises a spin-spin exchange catalyst, and wherein said composition has an osmolarity of 200-1400 mOsm/L; and then
generating, by MRI of the subject, an image of said body or body region,
whereby said MRI image in enhanced.

2. The method of claim 1, wherein said body region is a head, neck, thorax, abdomen, pelvis, limb(s), muscle, fat, or bone.

3. The method of claim 1, wherein said organ comprises an adrenal gland, pituitary, thymus, corpus *luteum*, retina, brain, spleen, lung, testicle, lymph nodes, liver, thyroid, small intestinal mucosa, leukocytes, pancreas, kidney, or salivary gland tissue.

4. The method of claim 1, wherein said body region is a brain.

5. The method of claim 1, wherein said body region is a heart.

6. The method of claim 1, wherein said administering step is carried out by intravenous administration.

7. The method of claim 1, wherein said administering step is carried out by intraperitoneal administration.

8. The method of claim 1, wherein said image comprises a T2 weighted image.

9. The method of claim 1, wherein said image comprises a metabolism image.

10. The method of claim 1, wherein said image comprises a perfusion image.

11. The method of claim 1, wherein the generating is performed during, or up to 5, 10, 30, 40, 60, 90 or 120 minutes after, or up to 1, 2, 3, or 4 hours after, parenterally administering the sterile aqueous composition.

12. The method of claim 1, wherein said spin-spin exchange catalyst is meglumine.

13. The method of claim 1, wherein said spin-spin exchange catalyst is a reducing sugar.

14. The method of claim 1, wherein said spin-spin exchange catalyst is a non-reducing sugar.

15. The method of claim 1, wherein said composition has an osmolarity of 200-1200 mOsm/L.

16. A method of enhancing a magnetic resonance imaging (MRI) image of a body or body region, or an organ or organ region in a subject, comprising:
parenterally administering to said subject in an MRI image-enhancing amount a sterile aqueous composition comprising:
100-600 mM ascorbate; and
100-600 mM of a combination of sodium and meglumine in a molar or millimolar (mM) ratio of from 10:90 to 90:10,
wherein said composition has an osmolarity of 200-1400 mOsm/L; and then
generating, by MRI of the subject, an image of said body or body region,
whereby said MRI image in enhanced.

17. The method of claim 16, wherein said body region is a head, neck, thorax, abdomen, pelvis, limb(s), muscle, fat, or bone.

18. The method of claim 16, wherein said organ comprises an adrenal gland, pituitary, thymus, corpus *luteum*, retina, brain, spleen, lung, testicle, lymph nodes, liver, thyroid, small intestinal mucosa, leukocytes, pancreas, kidney, or salivary gland tissue.

19. The method of claim 16, wherein said body region is a brain.

20. The method of claim 16, wherein said body region is a heart.

21. The method of claim 16, wherein said administering step is carried out by intravenous administration.

22. The method of claim 16, wherein said administering step is carried out by intraperitoneal administration.

23. The method of claim 16, wherein said image comprises a T2 weighted image.

24. The method of claim 16, wherein said image comprises a metabolism image.

25. The method of claim 16, wherein said image comprises a perfusion image.

26. The method of claim 16, wherein the generating is performed during, or up to 5, 10, 30, 40, 60, 90 or 120 minutes after, or up to 1, 2, 3, or 4 hours after, parenterally administering the sterile aqueous composition.

27. The method of claim 16, wherein said composition comprises meglumine ascorbate and sodium ascorbate in a molar or millimolar (mM) ratio of from 20:80 to 80:20.

28. The method of claim 16, wherein said composition comprises meglumine ascorbate and sodium ascorbate in a molar or millimolar (mM) ratio of from 30:70 to 70:30.

29. The method of claim 16, wherein said composition comprises meglumine ascorbate and sodium ascorbate in a molar or millimolar (mM) ratio of from 40:60 to 60:40.

\* \* \* \* \*

UNITED STATES PATENT AND TRADEMARK OFFICE
CERTIFICATE OF CORRECTION

PATENT NO. : 12,303,572 B2
APPLICATION NO. : 17/443863
DATED : May 20, 2025
INVENTOR(S) : Christopher David Lascola Page 1 of 1

It is certified that error appears in the above-identified patent and that said Letters Patent is hereby corrected as shown below:

In the Specification

Column 1, Line 20, STATEMENT OF GOVERNMENT SUPPORT: Please correct "W81XWH-Dec. 1, 0447" to read --W81XWH-12-1-0447--

Column 6, Line 36: Please correct "Asc.⁻" to read --Asc⁻--

Column 6, Line 37: Please correct "Asc.-" to read --Asc⁻--

Column 7, Line 15: Please correct "(N-methyl-D-glutamine)" to read --(N-methyl-D-glucamine)--

Column 9, Line 3: Please insert a paragraph break between "subjects." and "MRI"

Column 11, Line 42: Please correct "Pb" to read --$P_b$--

Column 11, Line 44: Please correct "stub" to read --$\delta\omega_b$--

Column 11, Line 47: Please correct "T" to read --$\tau$--

Signed and Sealed this
Sixteenth Day of September, 2025

Coke Morgan Stewart
*Acting Director of the United States Patent and Trademark Office*